(12) United States Patent
Roeder

(10) Patent No.: US 9,993,330 B2
(45) Date of Patent: Jun. 12, 2018

(54) ENDOLUMINAL PROSTHESIS SYSTEM

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 552 days.

(21) Appl. No.: 14/200,513

(22) Filed: Mar. 7, 2014

(65) Prior Publication Data
US 2014/0277348 A1 Sep. 18, 2014

Related U.S. Application Data

(60) Provisional application No. 61/779,650, filed on Mar. 13, 2013.

(51) Int. Cl.
*A61F 2/06* (2013.01)
*A61F 2/07* (2013.01)
*A61F 2/954* (2013.01)

(52) U.S. Cl.
CPC .............. *A61F 2/07* (2013.01); *A61F 2/954* (2013.01); *A61F 2002/061* (2013.01); *A61F 2002/067* (2013.01); *A61F 2002/075* (2013.01)

(58) Field of Classification Search
CPC ...... A61F 2/07; A61F 2/954; A61F 2002/075; A61F 2002/061; A61F 2002/067;
(Continued)

(56) References Cited

U.S. PATENT DOCUMENTS 4,902,508 A 2/1990 Badylak et al.
5,554,389 A 9/1996 Badylak et al.
(Continued)

FOREIGN PATENT DOCUMENTS

EP 2749249 A2 7/2014
WO WO 2006/028925 * 3/2006 ............... A61F 2/06
(Continued)

OTHER PUBLICATIONS

European Search Report for EP 14275054 dated Aug. 22, 2014 (6 pages).
(Continued)

*Primary Examiner* — Katherine M Shi
(74) *Attorney, Agent, or Firm* — Brinks Gilson & Lione

(57) ABSTRACT

An endoluminal prosthesis system may include a main graft and an extension graft. The main graft may include a tubular main body having a sidewall, open proximal and distal ends, a lumen, and a fenestration in the sidewall. The extension graft may include a tubular extension body, and tubular first and second extension legs. Each of the first and second extension legs may extend from the extension body and include a lumen in fluid communication with the extension body lumen. The extension graft may be deployable within the main graft such that the extension body extends through the fenestration in the sidewall of the main body. Each of the first and second extension legs may extend outward away from the main graft. An auxiliary guide such as an auxiliary cannula and/or auxiliary guide wire may be preloaded in the extension graft and extend through the lumen of each of the second extension leg and the extension body.

14 Claims, 15 Drawing Sheets

(58) Field of Classification Search
CPC ........ A61F 2250/006; A61F 2250/0062; A61F 2250/0063; A61F 2250/0064; A61F 2250/0065
See application file for complete search history.

(56) References Cited

U.S. PATENT DOCUMENTS

| | | | | |
|---|---|---|---|---|
| 5,676,697 | A * | 10/1997 | McDonald | A61F 2/90 623/1.35 |
| 5,720,735 | A * | 2/1998 | Dorros | A61F 2/90 604/284 |
| 5,993,844 | A | 11/1999 | Abraham et al. | |
| 6,099,567 | A | 8/2000 | Badylak et al. | |
| 6,206,931 | B1 | 3/2001 | Cook et al. | |
| 6,398,807 | B1 * | 6/2002 | Chouinard | A61F 2/90 623/1.35 |
| 6,908,477 | B2 * | 6/2005 | McGuckin, Jr. | A61F 2/07 128/898 |
| 7,407,509 | B2 * | 8/2008 | Greenberg | A61F 2/07 606/153 |
| 2005/0102018 | A1 | 5/2005 | Carpenter et al. | |
| 2005/0234542 | A1 * | 10/2005 | Melsheimer | A61F 2/07 623/1.35 |
| 2006/0184228 | A1 | 8/2006 | Khoury | |
| 2007/0106368 | A1 | 5/2007 | Vonderwalde | |
| 2008/0027533 | A1 * | 1/2008 | Oepen | A61F 2/856 623/1.35 |
| 2008/0269866 | A1 * | 10/2008 | Hamer | A61F 2/07 623/1.11 |
| 2009/0005847 | A1 * | 1/2009 | Adams | A61F 2/90 623/1.2 |
| 2009/0048663 | A1 * | 2/2009 | Greenberg | A61F 2/07 623/1.35 |
| 2009/0062898 | A1 * | 3/2009 | Das | A61F 2/954 623/1.11 |
| 2009/0171451 | A1 | 7/2009 | Kuppurathanam et al. | |
| 2011/0257731 | A1 * | 10/2011 | Hartley | A61F 2/07 623/1.35 |
| 2011/0313512 | A1 * | 12/2011 | Hartley | A61F 2/07 623/1.35 |
| 2012/0150273 | A1 * | 6/2012 | Centola | A61F 2/07 623/1.12 |
| 2012/0221094 | A1 * | 8/2012 | Cunningham | A61F 2/07 623/1.12 |
| 2013/0013050 | A1 * | 1/2013 | Shalev | A61F 2/07 623/1.13 |

FOREIGN PATENT DOCUMENTS

| | | | | |
|---|---|---|---|---|
| WO | WO 2006/028925 | A1 | 3/2006 | |
| WO | WO 2006/113501 | A1 | 10/2006 | |
| WO | WO 2011/100290 | A1 | 8/2011 | |
| WO | WO2013/074990 | * | 5/2013 | ............... A61F 2/07 |
| WO | WO 2013/074990 | A1 | 5/2013 | |

OTHER PUBLICATIONS

Examination Report for EP Application No. 14275054 dated Sep. 8, 2016, 6 pages.
Examination Report for EP Application No. 14275054.6 dated Jan. 18, 2018, 5 pages.

* cited by examiner

ENDOLUMINAL PROSTHESIS SYSTEM

RELATED APPLICATIONS

The present patent document claims the benefit of the filing date under 35 U.S.C. § 119(e) of Provisional U.S. Patent Application Ser. No. 61/779,650, filed Mar. 13, 2013, which is hereby incorporated by reference.

TECHNICAL FIELD

This disclosure relates to medical devices for implantation within the human or animal body for treatment of an endovascular condition. More particularly, it relates to an endoluminal prosthesis system adapted for treating a thoracic aorta of a patient.

BACKGROUND

Endovascular methods have been proposed for treatment of aneurysms of the aorta, particularly when an aneurysm is adjacent to the aortic bifurcation. But when an aneurysm occurs higher up in the aorta, for example, in the region of the descending aorta adjacent to the thoracic arch or in the ascending aorta, endovascular techniques for treating these aneurysms are somewhat more difficult because of the arched nature of the thoracic arch, the existence of major arteries in the region, and the proximity to the heart.

Generally, operations to treat aneurysms that include the ascending aorta or the arch have been done by open chest surgery. Such surgery generally involves surgical replacement of a portion of the aorta with a tubular prosthesis. Two foremost reasons for the risk associated with the procedure are difficulty of accessing the site of treatment and the potential for neural ischemia.

The surgical Bentall technique has been demonstrated with some success for treating ascending aortic aneurysms. But the Bentall technique may be used only in patients able to tolerate a fully surgical technique and thus is not suitable for patients that may be intolerant of such an invasive procedure.

In dealing with aortic arch aneurysms, procedural risk is greatly increased by inclusion of the brachiocephalic vessels and the aorta distal to the arch. The difficulty of the procedure also may be exacerbated by the necessity to provide branches to supply blood to the innominate, left common carotid, and subclavian arteries. Although surgical techniques have been successfully demonstrated to repair arch aneurysms, such techniques are highly invasive and have a high mortality rate, especially in high risk patients. Thus, such techniques are limited in utility.

SUMMARY

The present embodiments provide an endoluminal prosthesis and systems and methods for facilitating deployment of such a prosthesis.

In one example, an endoluminal prosthesis system may include a main graft and an extension graft. The main graft may include a tubular main body having a sidewall, an open proximal end, an open distal end, a lumen extending longitudinally between the proximal end and the distal end, and a fenestration in the sidewall. The extension graft may include a tubular extension body, a tubular first extension leg, and a tubular second extension leg. The extension body may include an open first end, a second end, and a lumen extending longitudinally between the first end and the second end. Each of the first extension leg and the second extension leg may extend from the extension body and include a first end, a second end, and a lumen in fluid communication with the lumen of the extension body. The extension graft may be deployable within the main graft such that the extension body extends through the fenestration in the sidewall of the main body. Each of the first extension leg and the second extension leg may extend outward away from the main graft.

In another example, an endoluminal prosthesis system may include a main graft and an extension graft. The main graft may include a tubular main body including a sidewall, an open proximal end, an open distal end, a lumen extending longitudinally between the proximal end and the distal end, and a fenestration in the sidewall. The extension graft may include a tubular extension body, a tubular first extension leg, and a tubular second extension leg. The extension body may include an open first end, a second end, and a lumen extending longitudinally between the first end and the second end. Each of the first extension leg and the second extension leg may extend from the extension body and include a first end, a second end, and a lumen in fluid communication with the lumen of the extension body. An auxiliary guide, such as a guide wire or a catheter or cannula, may be preloaded in the extension graft and extend through each of the lumen of the second extension leg and the lumen of the extension body. The extension graft may be positionable within the main graft such that the extension body extends through the fenestration in the sidewall of the main body, each of the first extension leg and the second extension leg extends outward away from the main graft, and an end or portion of the auxiliary guide is disposed within the lumen of the main graft.

In another example, a method of deploying a prosthesis system may include deploying a main graft. The main graft may include a tubular main body including a sidewall, an open proximal end, an open distal end, a lumen extending longitudinally between the proximal end and the distal end, and a fenestration in the sidewall. An extension graft may be deployed within the main graft. The extension graft may include a tubular extension body disposed within the fenestration of the main graft, a tubular first extension leg, and a tubular second extension leg. Each of the first extension leg and the second extension leg may extend from the extension body outward away from the main graft. An end of an auxiliary guide wire disposed within the lumen of the main graft may be snared. The auxiliary guide wire may extend through a lumen of the extension body and a lumen of the second extension leg. An introducer may be advanced over the end of the auxiliary guide wire and into the second extension leg. A branch extension graft may be deployed within the second extension leg with the introducer.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIG. 1 illustrates one example of a main graft.
FIG. 2 illustrates one example of an extension graft.
FIG. 3 illustrates a prosthesis system including the main graft of FIG. 1 and the extension graft of FIG. 2 deployed within a thoracic aorta of a patient.

DETAILED DESCRIPTION OF THE DRAWINGS AND THE PRESENTLY PREFERRED EMBODIMENTS

The present disclosure relates to an endoluminal prosthesis system for implantation within a human or animal body for repair of damaged vessels, ducts, or other physiological pathways and methods for delivering and deploying such an endoluminal prosthesis. The embodiments described in this disclosure will be discussed generally in relation to an endoluminal prosthesis system for deployment into the aortic arch, but the disclosure is not so limited and can be applied to other portions of the aorta or to other vasculature or other body vessels or lumens.

In the present disclosure, the term "proximal" refers to a direction that is generally closest to the heart during a medical procedure, while the term "distal" refers to a direction that is farthest from the heart during a medical procedure.

Figure 1:
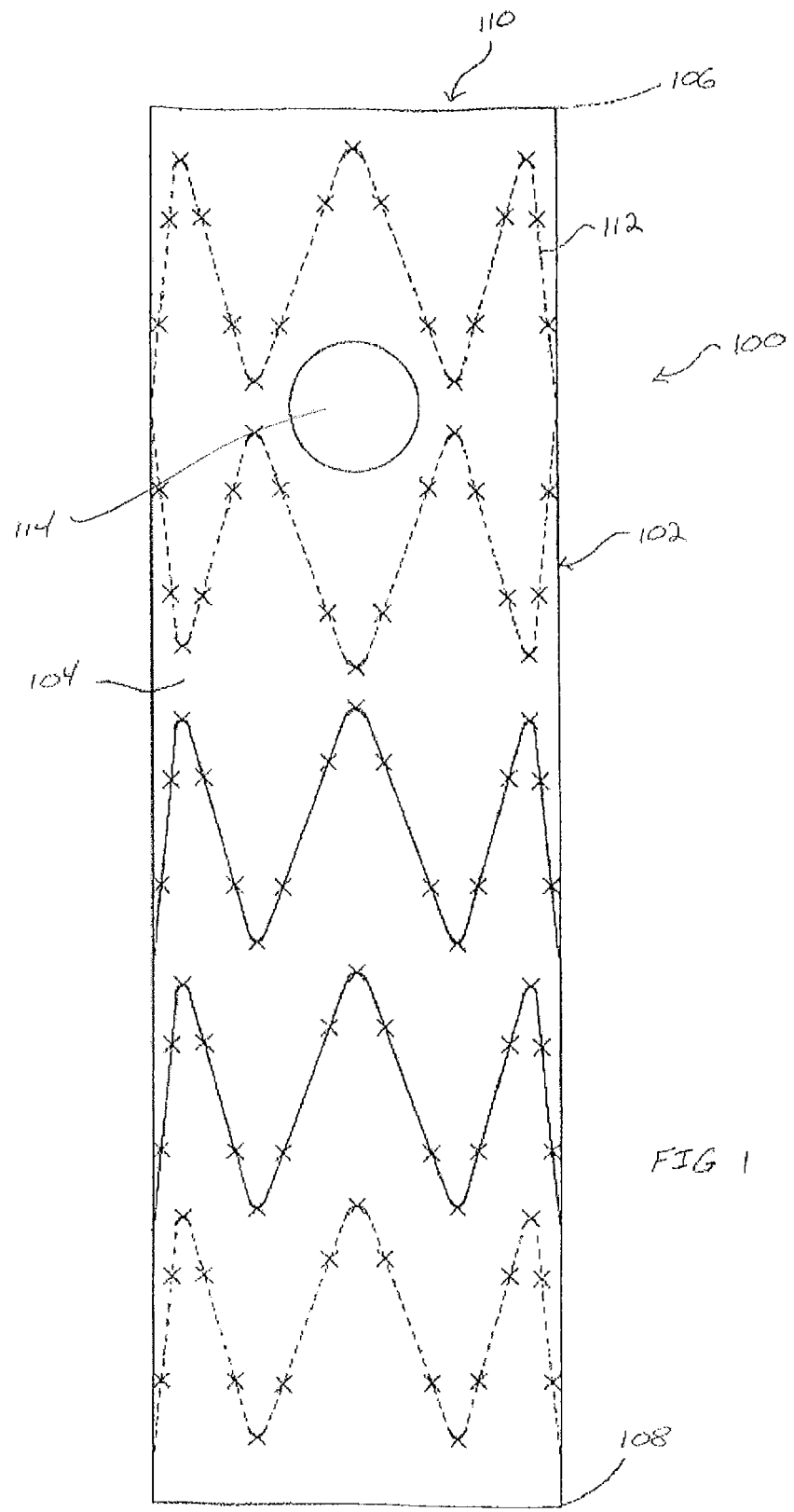
Figure 2:
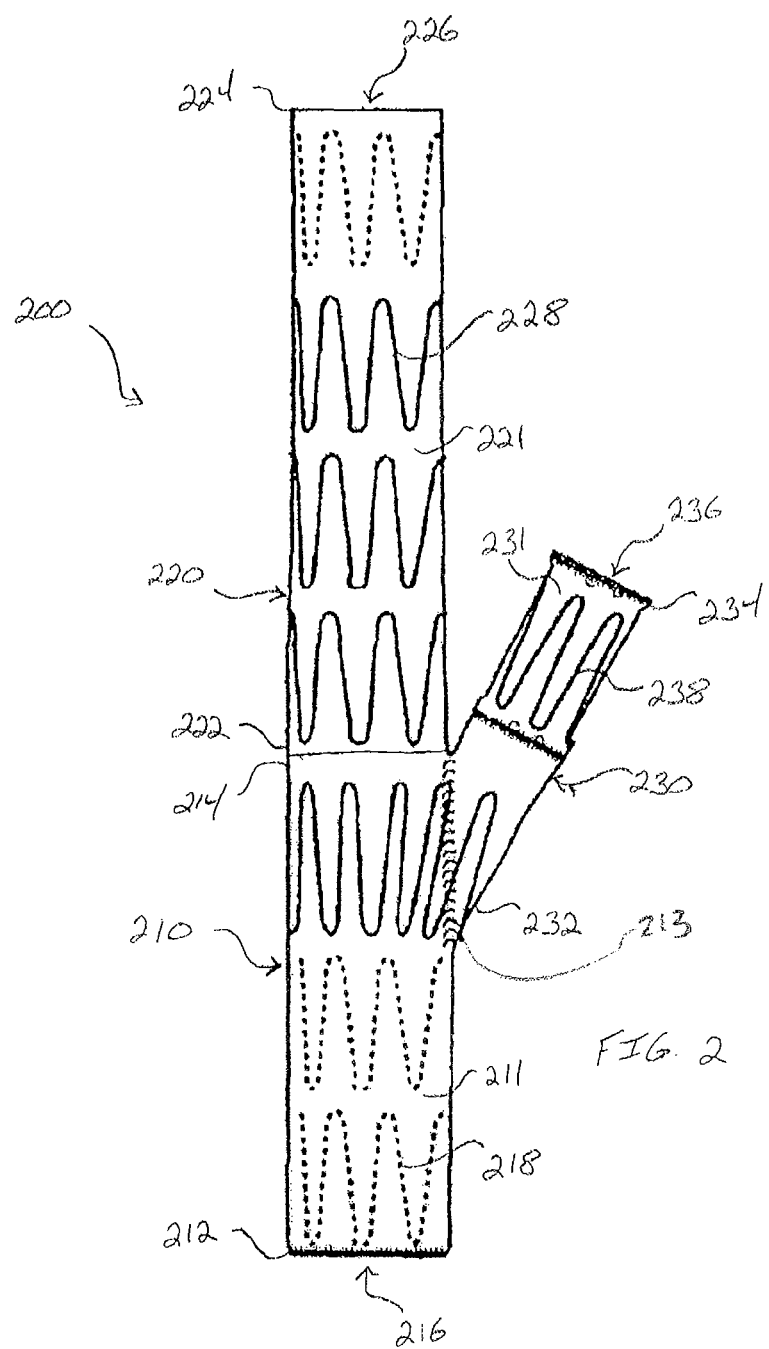

An endoluminal prosthesis system may include a main graft and an extension graft. FIG. 1 illustrates one example of a main graft 100, and FIG. 2 illustrates one example of an extension graft 200. The main graft may be configured for placement in an aortic arch as further described below. To that end, the main graft may be configured to extend from an ascending aorta, over the aortic arch, and into a descending aorta. The extension graft may be deployable within the main graft as further described below. To that end, the extension graft may be configured to extend from the main graft toward one or more branch vessels such as an innominate artery, a left common carotid artery, and/or a left subclavian artery.

As shown in FIG. 1, the main graft 100 may include a tubular main body 102 including a sidewall 104 of a biocompatible graft material. The main body 102 may include a proximal end opening at a proximal end 106, a distal end opening at a distal end 108, and a lumen 110 extending longitudinally within the main body. The main body 102 may include a support structure 112 attached to the sidewall 104 (e.g., attached to an inner surface and/or an outer surface of the sidewall). The main body 102 may include one or more fenestrations in the sidewall 104. For example, the main body 102 may include a fenestration 114 as shown in FIG. 1. The fenestration 114 may be configured as an opening through the sidewall 104 from the interior of the prosthesis to the exterior of the prosthesis. The fenestration 114 may have any suitable geometry including, for example, circular, semi-circular, oval, or oblong. The fenestration 114 may be positioned near the proximal end 106 of the main body 102.

Although the main body 102 is described herein as including one fenestration 114, this disclosure is not so limited. In other examples, the main body may include any number (e.g., one, three, or more) of fenestrations. For example, the main body may include two fenestrations as described below with reference to FIGS. 4-7. The number of fenestrations may be selected according to the number of branch vessels in the region in which the main graft is to be implanted as further described below. Additionally, or alternatively, the main body may include one or more tubular extensions extending from the one or more fenestrations as described below with reference to FIGS. 4-7.

The extension graft 200 may be configured as a branched or bifurcated graft. To that end, the extension graft 200 may include a tubular extension body 210, a tubular first extension leg 220, and a tubular second extension leg 230 as shown in FIG. 2. The extension body 210 may include a sidewall 211 of a biocompatible graft material. The extension body 210 may include a proximal end opening at a proximal end 212, a distal end opening at a distal end 214, and a lumen 216 extending longitudinally within the extension body. The extension body 210 may include a support structure 218 attached to the sidewall 211 (e.g., attached to an inner surface and/or an outer surface of the sidewall). The first extension leg 220 may include a sidewall 221 of a biocompatible graft material. The first extension leg 220 may include a proximal end opening at a proximal end 222, a distal end opening at a distal end 224, and a lumen 226 extending longitudinally within the first extension leg. The first extension leg 220 may include a support structure 228 attached to the sidewall 221 (e.g., attached to an inner surface and/or an outer surface of the sidewall). The second extension leg 230 may include a sidewall 231 of a biocompatible graft material. The second extension leg 230 may include a proximal end opening at a proximal end 232, a distal end opening at a distal end 234, and a lumen 236 extending longitudinally within the second extension leg. The second extension leg 230 may include a support structure 238 attached to the sidewall 231 (e.g., attached to an inner surface and/or an outer surface of the sidewall).

The extension body 210, the first extension leg 220, and/or the second extension leg 230 may be formed as a unitary structure or as two or more independent structures joined to one another to form the extension graft 200. For example, the extension body 210 and the first extension leg 220 may be formed as a unitary tubular structure, and the second extension leg 230 may be formed separately and joined to the unitary tubular structure to form the extension graft 200 as shown in FIG. 2. In other examples, the extension body, the first extension leg, and the second extension leg may be formed as a unitary structure, or each of the extension body, the first extension leg, and the second extension leg may be formed separately and joined to one another.

Each of the first extension leg 220 and the second extension leg 230 may extend from the extension body 210. For example, the first extension leg 220 may extend from the distal end 214 of the extension body 210 as shown in FIG. 2. Additionally, or alternatively, the second extension leg 230 may extend from the sidewall 211 of the extension body 210 as shown in FIG. 2. In other examples, both the first extension leg and the second extension leg may extend from the distal end of the extension body as described below with reference to FIG. 8. In other examples, both the first extension leg and the second extension leg may extend from the sidewall of the extension body or one of the first extension leg and the second extension leg may extend from the distal end of the extension body, and the other of the first extension leg and the second extension leg may extend from the sidewall of the extension body.

Returning to FIG. 2, the proximal end opening of the first extension leg 220 may be fluidly coupled to the distal end opening of the extension body 210. To that end, the proximal end 222 of the first extension leg 220 may be attached to the sidewall 211 of the extension body 210 adjacent to the distal end opening thereof such that the proximal end opening of the first extension leg is fluidly coupled to the distal end opening of the extension body. The lumen 226 of the first extension leg 220 may be in fluid communication with the lumen 216 of the extension body 210. In this manner, the lumen 216 of the extension body 210 and the lumen 226 of the first extension leg 220 may collectively form a continuous flow path between the proximal end 212 of the extension body and the distal end 224 of the first extension leg. The first extension leg 220 may extend distally from the distal end 214 of the extension body 210 as shown in FIG. 2. The first extension leg 220 may have a diameter that is substantially the same as a diameter of the extension body 210. The diameter of the first extension leg 220 may be substantially constant along the length thereof. Alternatively, the diameter of the first extension leg 220 may taper along the length thereof. For example, the diameter of the first extension leg 220 may decrease from a first diameter that is substantially the same as a diameter of the extension body 210 at the proximal end 222 to a second diameter at a position distal of the proximal end of the first extension leg. The second diameter may be smaller than the first diameter. For example, the extension body 210 may have a diameter sized to supply blood flow to two branch vessels, while the first extension leg 220 may have a smaller diameter sized to supply blood to one of the two branch vessels. Blood may be supplied to the other of the two branch vessels by the second extension leg 230 as described below. Alternatively, the second diameter may be larger than the first diameter. Additionally, or alternatively, the first extension leg 220 and the main body 210 may be coaxial with one another.

The extension body 210 may include a fenestration 213 in the sidewall 211 near the distal end 214 thereof. The proximal end opening of the second extension leg 230 may be fluidly coupled to the fenestration of the extension body 210. To that end, the proximal end 232 of the second extension leg 230 may be attached to the sidewall 211 of the extension body 210 adjacent to the fenestration thereof such that the proximal end opening of the second extension leg is fluidly coupled to the fenestration of the extension body. The lumen 236 of the second extension leg 230 may be in fluid communication with the lumen 216 of the extension body 210. In this manner, the lumen 216 of the extension body 210 and the lumen 236 of the second extension leg 230 may collectively form a continuous flow path between the proximal end 212 of the extension body and the distal end 234 of the second extension leg. The second extension leg 230 may extend distally and radially outward from the extension body 210 as shown in FIG. 2. The second extension leg 230 may extend away from the sidewall 211 of the extension body 210 and/or the sidewall 221 of the first extension leg 220 at any angle (e.g., an acute angle as shown in FIG. 2). Additionally, or alternatively, the second extension leg may extend circumferentially around the extension body and/or the first extension leg. For example, the second extension leg may extend at least partially around the extension body and/or the first extension leg in a spiral or helical configuration.

The second extension leg 230 may have a diameter that is smaller than a diameter of the extension body 210. For example, the extension body 210 may have a diameter sized to supply blood flow to two branch vessels, and the second extension leg 230 may have a smaller diameter sized to supply blood flow to one of the two branch vessels. Blood flow may be supplied to the other of the two branch vessels by the first extension leg 220 as described below. Alternatively, the second extension leg may have a diameter that is substantially the same or larger than the diameter of the extension body. The diameter of the second extension leg 230 may be substantially constant along the length thereof. Alternatively, the diameter of the second extension leg 230 may taper along the length thereof. For example, the diameter of the second extension leg 230 may taper from a first diameter at the proximal end 232 to a second diameter at a position distal of the proximal end of the second extension leg. The second diameter may be smaller than the first diameter. Alternatively, the second diameter may be larger than the first diameter.

The first extension leg 220 may extend farther distally than the second extension leg 230 as shown in FIG. 2. In other words, the distal end 224 of the first extension leg 220 may be positioned distal of the distal end 234 of the second extension leg 230. To that end, the first extension leg 220 may be longer than the second extension leg 230. This may enable the first extension leg 220 to extend into a first branch vessel while the second extension leg 230 extends toward, but not into a second branch vessel as described below. Alternatively, the second extension leg may extend farther distally than the first extension leg, or the first extension leg and the second extension leg may extend distally substantially the same distance.

Figure 3:
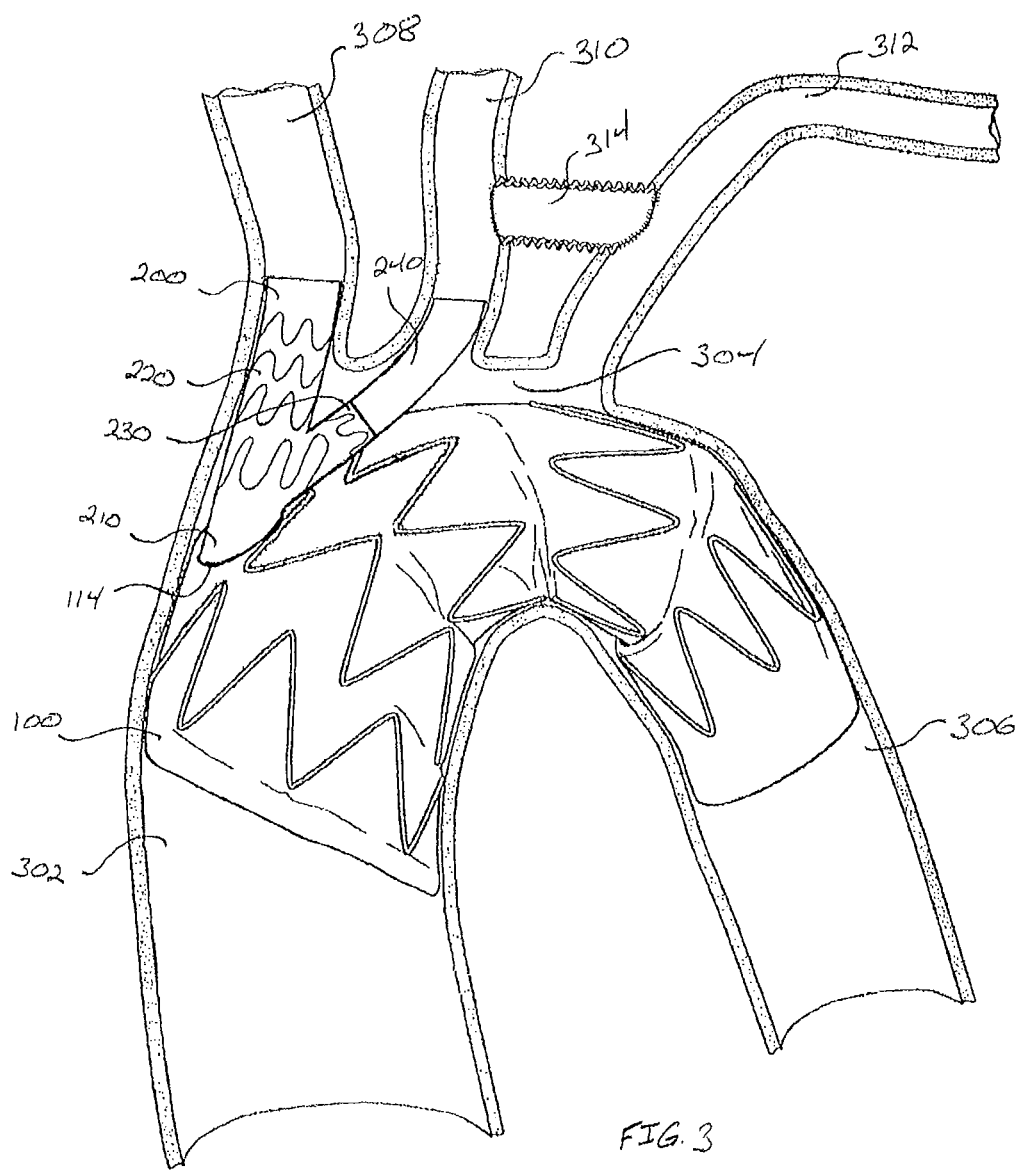

The main graft 100 may be configured for deployment within the thoracic arch as shown in FIG. 3. Upon deployment, the main graft 100 may extend from the ascending aorta 302, through the thoracic arch 304, and into the descending aorta 306. The main graft 100 may be deployed within the thoracic arch using any suitable endovascular technique such as, for example, that described below with reference to deployment of the main graft 400 as shown in FIGS. 10-15. Additionally, or alternatively, the extension graft 200 may be deployable within the main graft 100 as shown in FIG. 3. The extension graft 200 may be deployed within the main graft 100 using any suitable endovascular technique such as, for example, those described below with reference to deployment of the extension graft 500 as shown in FIGS. 10-15.

Upon deployment of the main graft 100 within the thoracic arch and deployment of the extension graft 200 within the main graft 100, the extension graft may be disposed within the fenestration 114 of the main graft as shown in FIG. 3. For example, the extension body 210 may extend through the fenestration 114 of the main graft 100 such that the proximal end 212 of the extension body is disposed within the lumen 110 of the main graft and the distal end 214 of the extension body is disposed external of the main graft. A portion of the sidewall 104 of the main body 102 adjacent to the fenestration 114 may be engaged by the exterior surface of the sidewall 211 of the extension body 210. In this manner, a substantially fluid-tight connection may be established between the main graft 100 and the extension graft 200 to inhibit fluid from leaking out of the prosthesis system at the interface between the main graft and the extension graft. The main graft may include a tubular extension coupled to the fenestration as described below with reference to FIGS. 4-7, which may increase the contact area between the main graft and the extension graft to further inhibit leakage of fluid from the prosthesis system.

One or more branch vessels may branch off of the aorta in the region of the thoracic arch 304. The branch vessels may include an innominate artery 308, a left common carotid artery 310, and a left subclavian artery 312 as shown in FIG. 3. The first extension leg 220 of the extension graft 200 may extend outward away from the main graft 100. The first extension leg 220 may extend toward a first branch vessel. The first extension leg 220 may extend a sufficiently long distance away from the main graft 100 to extend into the first branch vessel. For example, the first extension leg 220 may extend away from the main graft 100 and into the innominate artery 308 as shown in FIG. 3. In this manner, a continuous flow path may be established from the lumen 110 of the main graft 100 into the innominate artery 308 through the extension graft 200 (e.g., through the lumen 216 of the extension body 210 and the lumen 226 of the first extension leg 220). Alternatively, the first extension leg may extend a sufficiently short distance toward the first branch vessel such that the first extension leg does not enter the first branch vessel. A branch extension graft may be used to couple the first extension leg to the first branch vessel as described below. In other examples, the first extension leg may extend toward and/or into any other branch vessel.

The second extension leg 230 may extend outward away from the main graft 100. The second extension leg 230 may extend toward a second branch vessel. The second branch vessel may be positioned adjacent to the first branch vessel. The second extension leg 230 may extend a sufficiently short distance away from the main graft 100 such that the second extension leg does not enter the second branch vessel. For example, the second extension leg 230 may extend away from the main graft 100 toward the left common carotid artery 310 as shown in FIG. 3. A branch extension graft 240 may be used to couple the second extension leg 230 to the left common carotid artery 310 as described below. In this manner, a continuous flow path may be established from the lumen 110 of the main graft 100 into the left common carotid artery 310 through the extension graft 200 (e.g., through the lumen 216 of the extension body 210 and the lumen 236 of the second extension leg 230). Alternatively, the second extension leg may extend a sufficiently long distance toward the second branch vessel to extend into the second branch vessel. In other examples, the second extension leg may extend toward and/or into any other branch vessel.

The configuration of the extension graft 200 (e.g., the branched or bifurcated configuration) may enable the extension graft to be deployed within the main graft 100 to fluidly couple the main graft to two branch vessels (e.g., two adjacent branch vessels) through a single fenestration 114. This may reduce the amount of time which may be required to couple the main graft to the two branch vessels (e.g., because a single extension graft may be used to couple the main graft to the two branch vessels instead of deploying two *separate* extension grafts within the main graft).

The main graft 100 may block and/or substantially prevent blood flow from the thoracic arch 304 into the left subclavian artery 312 as shown in FIG. 3. To maintain blood flow into the left subclavian artery 312, an anastomosis 314 may be provided between the left common carotid artery 310 and the left subclavian artery 312. The anastomosis 314 may be provided using any suitable technique. For example, the anastomosis 314 may be provided in a preparatory operation prior to deployment of the prosthesis system.

Figure 4:
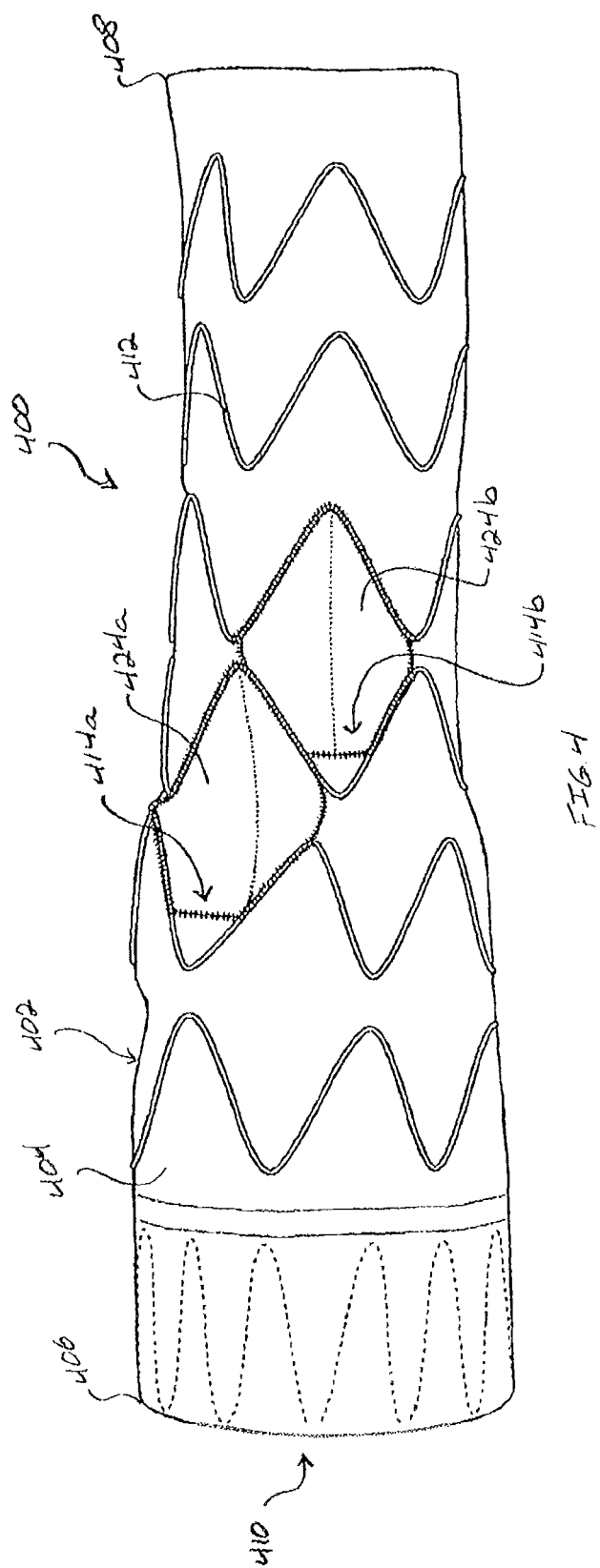
FIG. 4 illustrates one example of a main graft.

FIG. 4 illustrates another example of a main graft 400. The main graft 400 may be configured generally as described in International Patent App. Pub. No. WO 2011/100290, which is incorporated by reference herein in its entirety. The main graft 400 may include a tubular main body 402 including a sidewall 404 of a biocompatible graft material. The main body 402 may include a proximal end opening at a proximal end 406, a distal end opening at a distal end 408, and a lumen 410 extending longitudinally within the main body. The main body 402 may include a support structure 412 attached to the sidewall 404. The main body 402 may include one or more fenestrations in the sidewall 404. For example, the main body 402 may include a first fenestration 414a and a second fenestration 414b as shown in FIG. 4.

Figure 5:
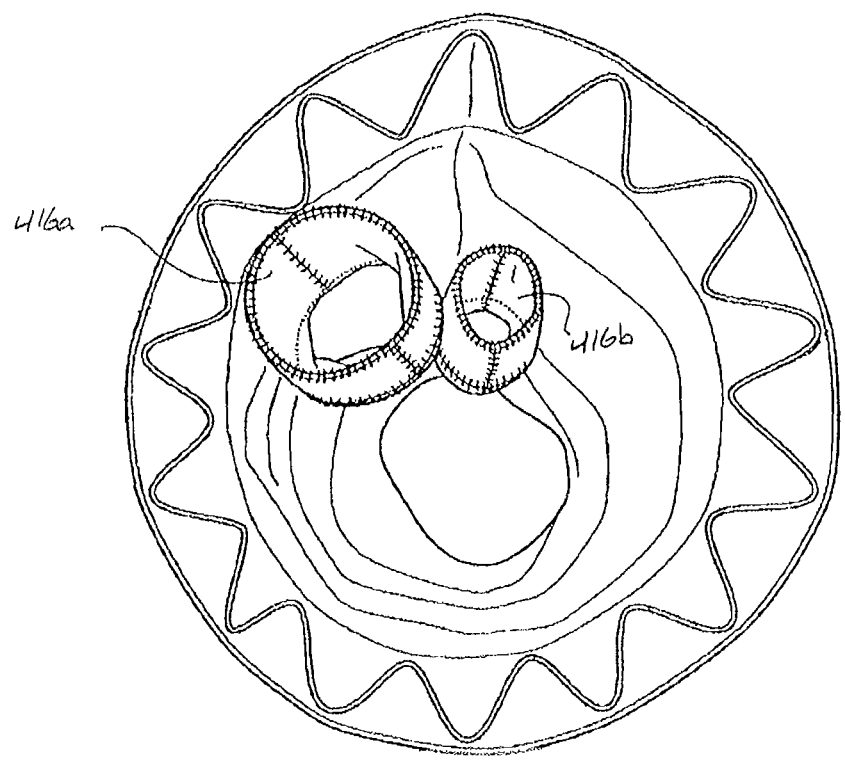
FIG. 5 illustrates a view into the lumen of the main graft of FIG. 4 from the proximal end opening.
Figure 6:
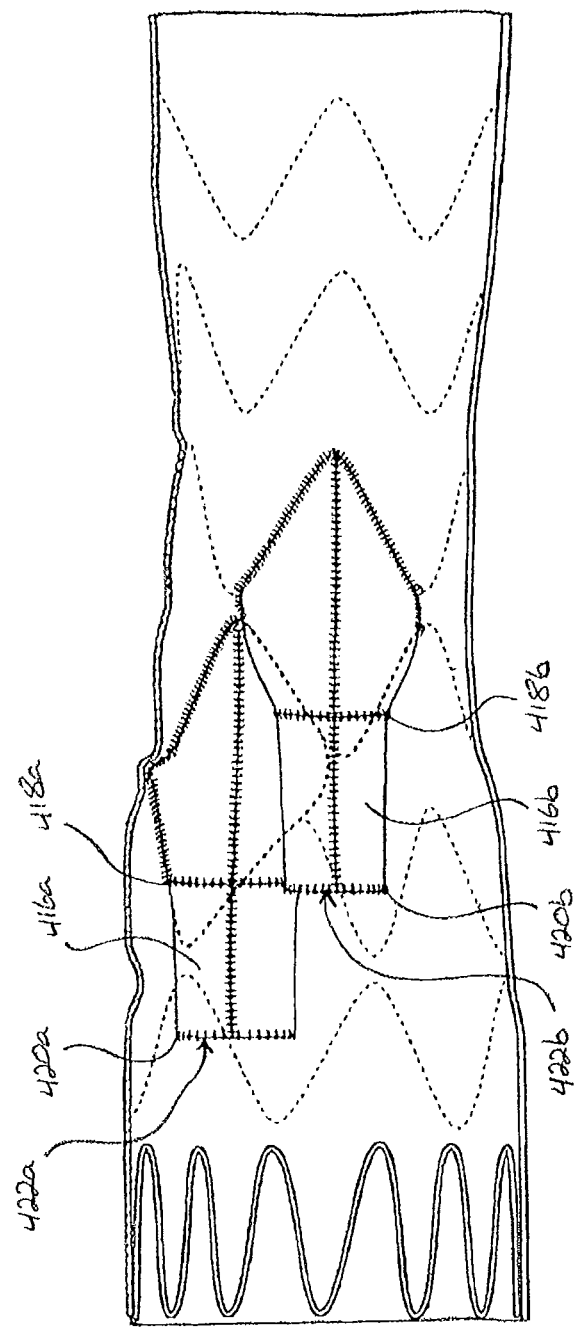
FIG. 6 illustrates a longitudinal cross sectional view of the main graft of FIG. 4.

FIG. 5 illustrates a view into the lumen 410 of the main body 402 from the proximal end 406, and FIG. 6 illustrates a longitudinal cross sectional view of the main graft 400. The main graft 400 may include one or more tubular extensions extending from the sidewall 404. For example, the main graft 400 may include a first tubular extension 416a and a second tubular extension 416b as shown in FIGS. 5-6. Although the main graft 400 is described herein as including two fenestrations and two tubular extensions, this disclosure is not so limited. In other examples, the main graft may include any number (e.g., one, three, or more) of fenestrations and any number (e.g., one, three, or more) of tubular extensions. The number of tubular extensions may be the same as or different than the number of fenestrations. For example, a tubular extension may be coupled to each fenestration as shown in FIGS. 5-6 and further described below. Alternatively, one or more fenestrations may be free of a corresponding tubular extension. The number of fenestrations and/or tubular extensions may be selected according to the number of branch vessels in the region in which the main graft is to be implanted.

The first tubular extension 416a may include a first end 418a, a second end 420a, and a lumen 422a extending longitudinally within the first tubular extension. The first tubular extension 416a may be fluidly coupled to the first fenestration 414a. To that end, the first end 418a may be coupled to the sidewall 404 adjacent to the first fenestration 414a such that the lumen 422a of the first tubular extension 416a is in fluid communication with the first fenestration 414a. The first tubular extension 416a may be disposed within the lumen 410 of the main body 402. The first tubular extension 416a may extend proximally from the sidewall 404 toward the proximal end 406 of the main body 402 as shown in FIGS. 5-6. Alternatively, the first tubular extension may extend distally from the sidewall.

The second tubular extension 416b may include a first end 418b, a second end 420b, and a lumen 422b extending longitudinally within the second tubular extension. The second tubular extension 416b may be fluidly coupled to the second fenestration 414b. To that end, the first end 416b may be coupled to the sidewall 404 adjacent to the second fenestration 414b such that the lumen 422b of the second tubular extension 416b is in fluid communication with the second fenestration 414b. The second tubular extension 416b may be disposed within the lumen 410 of the main body 402. The second tubular extension 416b may extend proximally from the sidewall 404 toward the proximal end 406 of the main body 402 as shown in FIGS. 5-6. Alternatively, the second tubular extension may extend distally from the sidewall.

The first tubular extension 416a and the second tubular extension 416b may be disposed adjacent to one another as shown in FIGS. 5-6. The first tubular extension 416a and/or the second tubular extension 416b may be formed from a biocompatible graft material, which may be the same as or different than the biocompatible graft material of the sidewall 404. The first tubular extension 416a and/or the second tubular extension 416b may be formed integrally with the sidewall 404. Alternatively, the first tubular extension 416a and/or the second tubular extension 416b may be formed separately and attached to the sidewall 404 (e.g., by sutures, adhesive, staples, clips, or any other suitable attachment mechanism). The first tubular extension 416a and/or the second tubular extension 416b may include a support structure.

The main body 402 may include one or more recesses in the sidewall 404. For example, the main body 402 may include a first recess 424a and a second recess 424b as shown in FIG. 4. Each recess may be configured as a dimple or depression in the sidewall 402. To that end, each recess may be positioned between adjacent struts and bends of the support structure 412 (e.g., openings in the support structure). Each recess may extend inward into the lumen 410 of the main body 402. The first recess 424a and/or the second recess 424b may be formed integrally with the sidewall 404. Alternatively, the first recess 424a and/or the second recess 424b may be formed separately and attached to the sidewall 404 (e.g., by sutures, adhesive, staples, clips, or any other suitable attachment mechanism).

The first fenestration 414a may be positioned within the first recess 424a as shown in FIG. 4. Additionally, or alternatively, the second fenestration 414b may be positioned within the second recess 424b. The first tubular extension 416a may extend from the first recess 424a as shown in FIGS. 5-6. Additionally, or alternatively, the second tubular extension 416b may extend from the second recess 424b. Upon deployment of the main graft 400, the recesses may provide space between the sidewall 404 and the body vessel wall to aid in deployment of the extension graft as further described below. Although the main graft 400 is described herein as including two recesses, this disclosure is not so limited. In other examples, the main graft may include any number (e.g., one, three, or more) of recesses. The number of recesses may be the same as or different than the number of fenestrations.

Figure 7:
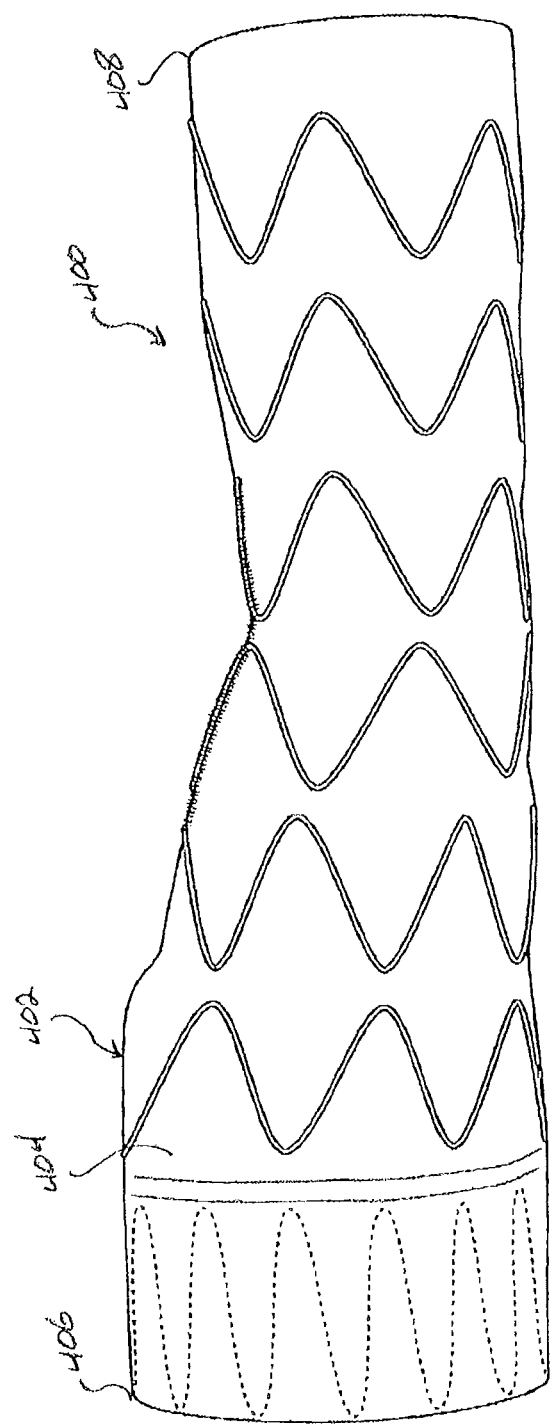
FIG. 7 illustrates the main graft of FIG. 4.

The main body 402 of the main graft 400 may be tapered as shown in FIG. 7. For example, the diameter of the main body 402 may decrease in a proximal to distal longitudinal direction along at least a portion of the length of the main body. In one example, the main body 402 may have a diameter of between about 35 mm and about 50 mm near the proximal end 406 and/or a diameter of between about 30 mm and about 40 mm near the distal end 408. In other examples, the main body 402 may have any suitable diameter (e.g., for placement within any suitable body vessel). An intermediate portion of the main body 402 may taper from a first diameter to a second diameter in the proximal to distal longitudinal direction. The first diameter may be larger than the second diameter as shown in FIG. 7. Alternatively, the first diameter may be smaller than the second diameter. The fenestrations and/or the recesses may be positioned within the intermediate portion of the main body 402 as shown in FIGS. 4-7.

Figure 8:
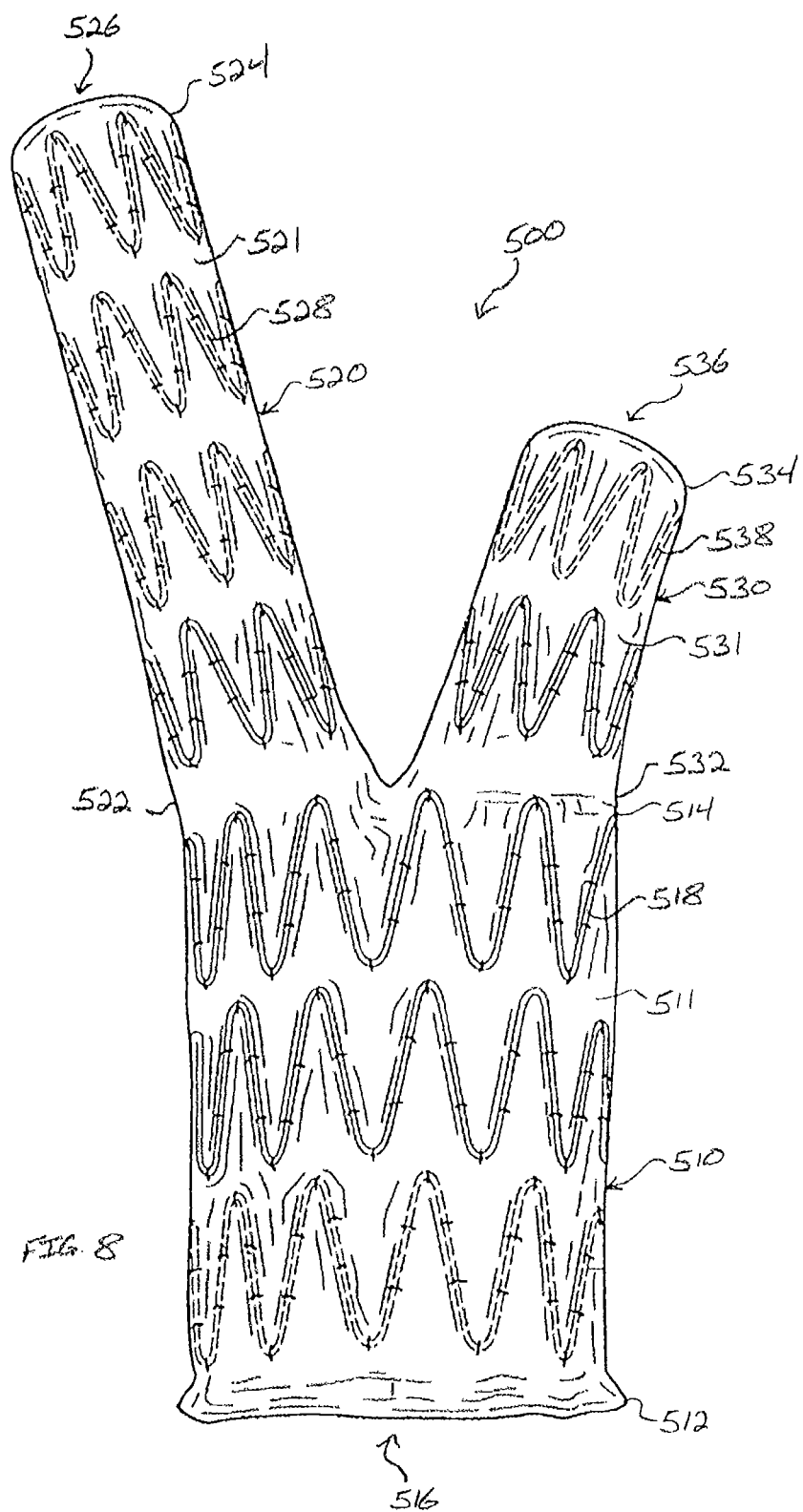
FIG. 8 illustrates one example of an extension graft.

FIG. 8 illustrates another example of an extension graft 500. The extension graft 500 may be similar to the extension graft 200 described above with reference to FIG. 2. For example, the extension graft 500 may include a tubular extension body 510, a tubular first extension leg 520, and a tubular second extension leg 530. The extension body 510 may include a sidewall 511 of a biocompatible graft material. The extension body 510 may include a proximal end opening at a proximal end 512, a distal end opening at a distal end 514, and a lumen 516 extending longitudinally within the extension body. The extension body 510 may include a support structure 518 attached to the sidewall 511 (e.g., attached to an inner surface and/or an outer surface of the sidewall). The first extension leg 520 may include a sidewall 521 of a biocompatible graft material. The first extension leg 520 may include a proximal end opening at a proximal end 522, a distal end opening at a distal end 524, and a lumen 526 extending longitudinally within the first extension leg. The first extension leg 520 may include a support structure 528 attached to the sidewall 521 (e.g., attached to an inner surface and/or an outer surface of the sidewall). The second extension leg 530 may include a sidewall 531 of a biocompatible graft material. The second extension leg 530 may include a proximal end opening at a proximal end 532, a distal end opening at a distal end 534, and a lumen 536 extending longitudinally within the second extension leg. The second extension leg 530 may include a support structure 538 attached to the sidewall 531 (e.g., attached to an inner surface and/or an outer surface of the sidewall). The extension body 510, the first extension leg 520, and/or the second extension leg 530 may be formed as a unitary structure or as two or more independent structures joined to one another to form the extension graft 500.

Each of the first extension leg 520 and the second extension leg 530 may extend from the extension body 510. For example, each of the first extension leg 520 and the second extension leg 530 may extend from the distal end 514 of the extension body 510 as shown in FIG. 8. To that end, each of the proximal end opening of the first extension leg 520 and the proximal end opening of the second extension leg 230 may be fluidly coupled to the distal end opening of the extension body 510. The first extension leg 520 and the second extension leg 530 of the prosthesis 500 may be positioned adjacent to one another with each of the proximal end 522 of the first extension leg and the proximal end 532 of the second extension leg attached to the distal end 514 of the extension body 510. The first extension leg 520 may extend from the extension body 510 in a first direction to a first side of the extension body, and the second extension leg 530 may extend from the extension body in a second direction to a second side of the extension body opposite the first side as shown in FIG. 8. In one example, the first extension leg 520 and the second extension leg 530 may extend from the extension body 510 such that the extension graft 500 is substantially "Y" shaped, with the first extension leg and the second extension leg forming the arms of the "Y" shape as shown in FIG. 8. In other words, the first extension leg 520 and the second extension leg 530 may extend away from the extension body 510 and one another to form the arms of the "Y" shape. In this manner, the extension graft 500 may be configured as a bifurcated prosthesis. In one example, the proximal end 522 of the first extension leg 520 may be attached to the proximal end 532 of the second extension leg 530 (e.g., at the intersection of the two arms of the "Y" shape) at a bifurcation.

The lumen 526 of the first extension leg 520 and/or the lumen 536 of the second extension leg 530 may be in fluid communication with the lumen 516 of the extension body 510 to form a continuous flow path between the proximal end 512 of the extension body and the distal end 524 of the first extension leg and/or the distal end 534 of the second extension leg. The first extension leg 520 and/or the second extension leg 530 may have a diameter that is smaller than a diameter of the extension body 510. For example, the extension body 510 may have a diameter sized to supply blood flow to two branch vessels, and the first extension leg 520 and/or the second extension leg 530 may have a smaller diameter sized to supply blood flow to one of the two branch vessels. Alternatively, the first extension leg and/or the second extension leg may have a diameter that is substantially the same or larger than the diameter of the extension body. The diameter of the first extension leg 520 and/or the second extension leg 530 may be substantially constant along the length thereof. Alternatively, the diameter of the first extension leg and/or the second extension leg may taper along the length thereof.

The first extension leg 520 may extend farther distally than the second extension leg 530 as shown in FIG. 8. To that end, the first extension leg 520 may be longer than the second extension leg 530. This may enable the first extension leg 520 to extend into a first branch vessel while the second extension leg 530 extends toward, but not into a second branch vessel as described below. Alternatively, the second extension leg may extend farther distally than the first extension leg, or the first extension leg and the second extension leg may extend distally substantially the same distance.

Figure 9:
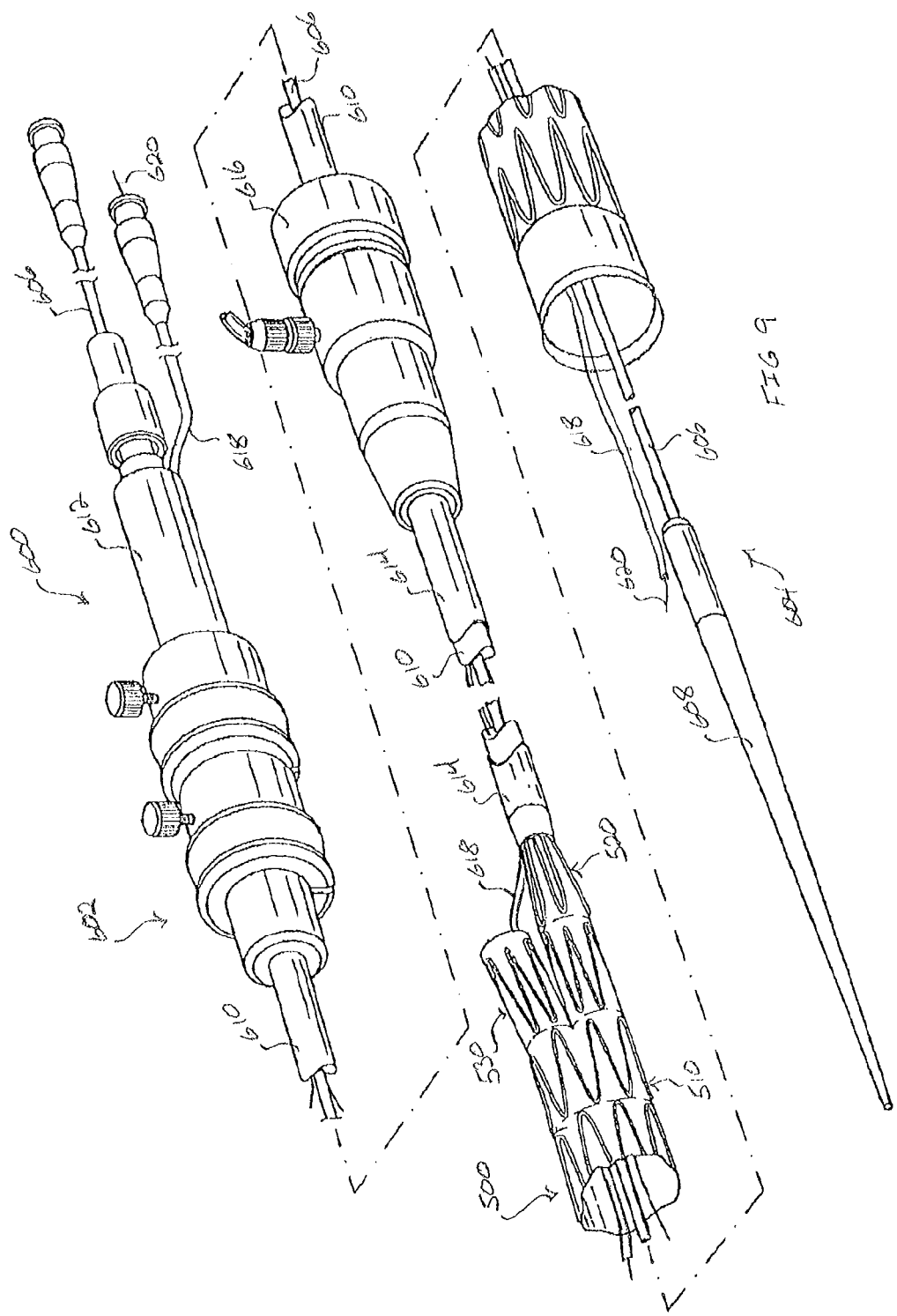
FIG. 9 illustrates one example of an introducer with the extension graft of FIG. 8 loaded thereon.

The extension graft 500 may be deployable within the main graft 400 as further described below. To that end, the extension graft 500 may be deployed using any suitable introducer or delivery device. FIG. 9 illustrates one example of an introducer 600 that may be used to deploy the extension graft 500. The introducer 600 may include a first portion 602 configured to remain outside of a patient and a second portion 604 configured for introduction into the patient during use. The introducer 600 may include an elongate tubular inner cannula 606 (e.g., a guide wire cannula) extending longitudinally along the length of the introducer. A connector (e.g., a Luer Lock fitting) may be positioned at a first end of the inner cannula 606 and/or a tip 608 (e.g., a dilator tip) may be positioned at a second end of the inner cannula opposite the first end. The introducer 600 may include an elongate tubular outer cannula 610 (e.g., a pusher cannula) about the inner cannula 606. A handle 612 may be positioned at a first end of the outer cannula 610. The outer cannula 610 may extend from the first end toward the tip 608 to a second end opposite the first end. The introducer 600 may include an elongate tubular sheath 614 about the inner cannula 606 and/or the outer cannula 610. A sheath hub 616 may be positioned at a first end of the sheath 614. The sheath 614 may extend from the first end toward the tip 608 to a second end opposite the first end. The sheath 614 may be longitudinally movable relative to the inner cannula 606 and/or the outer cannula 610. For example, the sheath 614 may be retracted toward the handle 612 (e.g., by moving the sheath hub 616) to enable at least partial expansion of the extension graft 500 as further described below.

The extension graft 500 may be loaded on the introducer 600 such that the inner cannula 606 extends through the lumen 526 of the first extension leg 520 and the lumen 516 of the extension body as shown in FIG. 6. The extension graft 500 may be positioned on the introducer 600 such that the distal end 524 of the first extension leg 520 is directed toward the handle 612 (e.g., toward the first end of the introducer). Additionally, or alternatively, the distal end 534 of the second extension leg 530 may be directed toward the handle 612 (e.g., toward the first end of the introducer 600). Additionally, or alternatively, the proximal end 512 of the extension body 510 may be directed toward the tip 608 (e.g., toward the second end of the introducer 600).

The introducer 600 may include an elongate tubular auxiliary cannula 618 as shown in FIG. 9. The auxiliary cannula 618 may extend longitudinally along the length of the introducer 600. A connector (e.g., a Luer Lock fitting) may be positioned at a first end of the auxiliary cannula 618. The auxiliary cannula 618 may extend from the first end toward the tip 608 to a second end opposite the first end. In one example, the second end of the auxiliary cannula may be positioned adjacent to the tip 608 as shown in FIG. 9. The auxiliary cannula 618 may be positioned within the outer cannula 610 and/or the sheath 614. In one example, the auxiliary cannula 618 may be positioned within the outer cannula 610 adjacent to the inner cannula 606. The auxiliary cannula 618 may extend from the first end through the handle 612 and into the outer cannula 610. The auxiliary cannula 618 may extend through the outer cannula 610 and out through the second end of the outer cannula. The auxiliary cannula 618 may enter the extension graft 500 through the distal end opening at the distal end 534 of the second extension leg 530 as shown in FIG. 9. The auxiliary cannula 618 may extend through the second extension leg 530 into the extension body 510 and exit the extension graft 500 through the proximal end opening at the proximal end 512 of the extension body. The auxiliary cannula 618 may extend away from the extension graft 500 to the second end adjacent to the tip 608 as shown in FIG. 9.

An auxiliary guide wire 620 may be disposed within the auxiliary cannula 618. The auxiliary guide wire 620 may aid in deploying a branch extension graft within the second extension leg 530 of the extension graft 500 as further described below. To that end, the auxiliary guide wire 620 may extend from a first end toward the tip 608. For example, the auxiliary guide wire 620 may enter the first end of the auxiliary cannula 618 (e.g., through the connector), extend longitudinally within the auxiliary cannula, and exit the second end of the auxiliary cannula. In this manner, the auxiliary guide wire 620 may extend from the first end through the handle 612 and into the outer cannula 610. The auxiliary guide wire 620 may extend through the outer cannula 610 and out through the second end of the outer cannula. The auxiliary guide wire 620 may enter the extension graft 500 through the distal end opening at the distal end 534 of the second extension leg 530. The auxiliary guide wire 620 may extend through the second extension leg 530 into the extension body 510 and exit the extension graft 500 through the proximal end opening at the proximal end 512 of the extension body. The auxiliary guide wire 620 may extend away from the extension graft 500 and exit the second end of the auxiliary cannula 618 as shown in FIG. 9. The auxiliary guide wire 620 may be longitudinally movable relative to the auxiliary cannula 620. For example, the auxiliary guide wire 620 may be advanced relative to the auxiliary cannula 620 to extend the second end of the auxiliary guide wire farther beyond the second end of the auxiliary cannula. Additionally, or alternatively, the auxiliary guide wire 620 may be retracted relative to the auxiliary cannula 618 to withdraw a portion of the auxiliary guide wire (e.g., the second end of the auxiliary guide wire) into the auxiliary cannula 618. The auxiliary cannula 618 and/or the auxiliary guide wire 620 may be preloaded through the extension graft 500 as described herein. In this manner, the auxiliary cannula 618 and/or the auxiliary guide wire 620 may aid in deploying a branch extension graft within the second extension leg 530 as further described below.

The introducer 600 may be configured as part of a low profile delivery system. To that end, the auxiliary guide wire 620 may be configured as a 0.035 in wire or a 0.018 in wire (e.g., a wire having a diameter of about 0.035 in or about 0.018 in). Additionally, or alternatively, the auxiliary cannula 618 may be configured as a 4 Fr catheter or a 3 Fr catheter. Additionally, or alternatively, the sheath 614 may have size of less than about 16 Fr, preferably less than about 14 Fr. In other examples, the auxiliary guide wire, the auxiliary cannula, and/or the sheath may have any suitable size.

Figure 10:
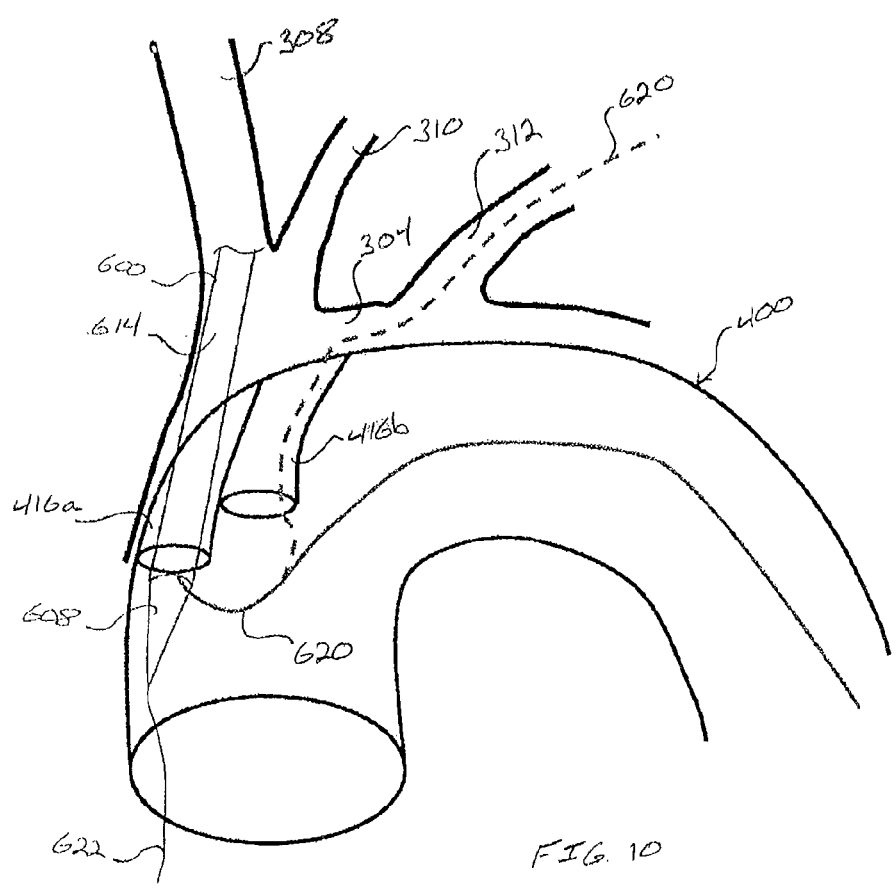
FIG. 10 illustrates the main graft of FIG. 4 deployed within a thoracic aorta of a patient.

FIGS. 10-13 illustrate exemplary steps for deployment of the prosthesis system, including the main graft 400 and the extension graft 500, within the thoracic aorta. Deployment of the prosthesis system including the main graft 100 and the extension graft 200 shown in FIGS. 1-3 may be performed in a similar manner. The main graft 400 may be deployed within the thoracic aorta using any suitable endovascular technique. For example, the main graft 400 may be compressed into a reduced diameter configuration and loaded onto an introducer. After being positioned within the thoracic aorta, the main graft 400 may be released from the introducer (e.g., by retraction of a sheath of the introducer and/or manipulation of one or more trigger wires or other retention mechanism) to expand and engage the walls of the thoracic aorta. Upon deployment, the main graft 400 may extend from the ascending aorta 302, through the thoracic arch 304, and into the descending aorta 306 as shown in FIG. 10. For clarity, FIG. 10 shows a cutaway view of the main graft 400 so that the tubular extensions disposed within the lumen 410 are visible.

The extension graft 500 may be deployable within the main graft 400. The extension graft 500 may be deployed using any suitable endovascular technique. For example, a guide wire 622 may be introduced into the innominate artery 308 (e.g., via the axillary artery or the right carotid artery) and advanced proximally within the innominate artery. The guide wire 622 may be advanced proximally through the first fenestration 414a and the first tubular extension 416a of the main graft 400. The guide wire 622 may be further advanced proximally within the lumen 410 of the main graft, out through the proximal end opening, and into the descending aorta 302 as shown in FIG. 10.

The extension graft 500 may be loaded onto the introducer 600 as described above. The introducer 600 may be introduced over the guide wire 622 and advanced proximally through the innominate artery 308. The introducer 600 may be advanced further proximally through the first fenestration 414a and the first tubular extension 416a of the main graft 400 such that the tip 608 of the introducer is disposed within the lumen 410 of the main graft 400 as shown in FIG. 10. The auxiliary guide wire 620 may extend proximally beyond the second end of the sheath 614, which may be positioned in the delivery configuration (e.g., abutting the tip 608). In this manner, the second end of the auxiliary guide wire 620 may be exposed outside of the sheath 614. The auxiliary guide wire 620 may be snared. For example, a snare may be introduced into the thoracic aorta (e.g., via the femoral artery) to snare the second end of the auxiliary guide wire 620. The second end of the auxiliary guide wire 620 may be pulled distally through the lumen 410 of the main graft 400 and out through the distal end opening at the distal end 408 of the main graft. This path of the auxiliary guide wire 620 is shown as a solid line in FIG. 10. The second end of the auxiliary guide wire 620 may be pulled out of the patient's body via the femoral artery. In this manner, the auxiliary guide wire 620 may serve as a through wire with both of the first end and the second end of the auxiliary guide wire positioned outside of the patient's body (e.g., the first end via the axillary artery or the right carotid artery and the second end via the femoral artery). The auxiliary guide wire 620 may be preloaded in the second extension leg 530 as described above. This may enable deployment of a branch extension graft within the second extension leg 530 as further described below. With the auxiliary guide wire 620 in place, the auxiliary sheath 618, if used, may be retracted over the auxiliary guide wire and removed from the patient's body (e.g., via the axillary artery or the right carotid artery).

In another example, the snare may be introduced into the thoracic aorta via the left subclavian artery 312 to snare the second end of the auxiliary guide wire 620. The second end of the auxiliary guide wire 620 may be pulled distally through the second tubular extension 416b and out through the second fenestration 414b of the main graft 400. This path of the auxiliary guide wire 620 is shown as a dashed line in FIG. 10. The second end of the auxiliary guide wire 620 may be pulled out of the patient's body via the left subclavian artery. In this manner, the auxiliary guide wire 620 may serve as a through wire with both of the first end and the second end of the auxiliary guide wire positioned outside of the patient's body (e.g., the first end via the axillary artery or the right carotid artery and the second end via the left subclavian artery). This may enable deployment of a branch extension graft within the extension graft 500 as further described below.

In another example, the snare may be introduced into the thoracic aorta via the apex of the left ventricle to snare the second end of the auxiliary guide wire 620. The second end of the auxiliary guide wire 620 may be pulled proximally through the proximal end opening of the main graft 400 and out of the patient's body via the left ventricle. In this manner, the auxiliary guide wire 620 may serve as a through wire with both of the first end and the second end of the auxiliary guide wire positioned outside of the patient's body (e.g., the first end via the axillary artery or the right carotid artery and the second end via the left ventricle).

Figure 11:
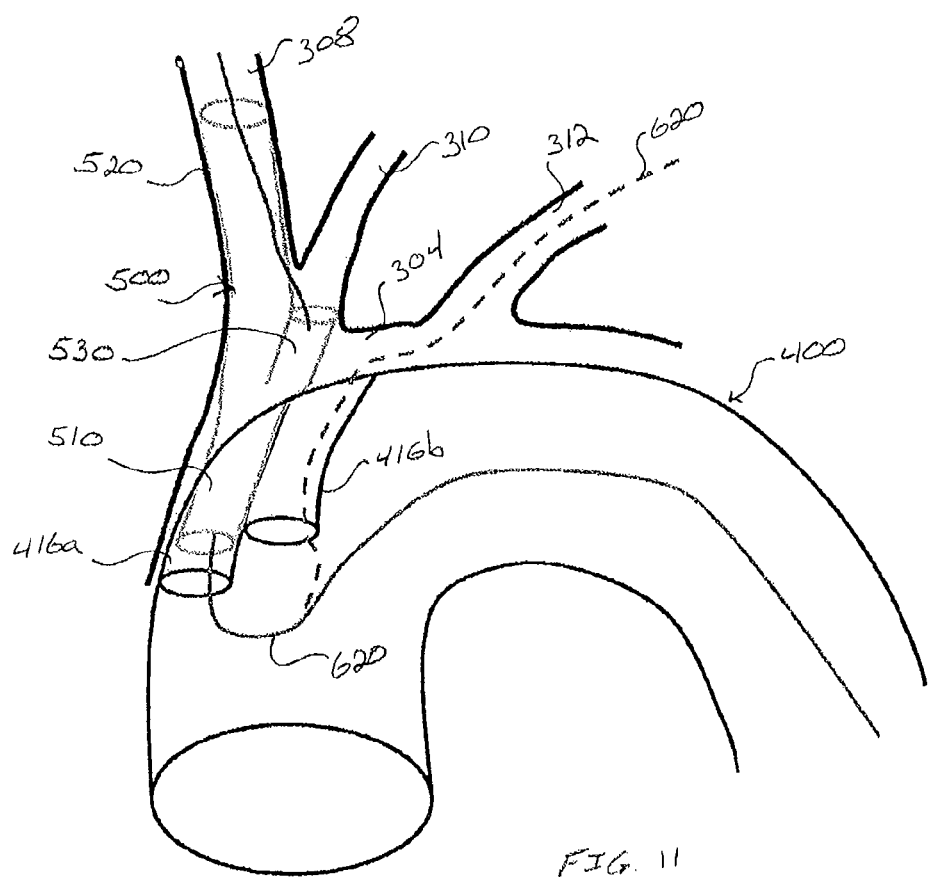
FIG. 11 illustrates one example of the extension graft of FIG. 8 deployed within the main graft of FIG. 10.

The extension graft 500 may be deployed within the main graft 400. The sheath 614 of the introducer 600 may be at least partially retracted to expose at least a portion of the extension graft 500. For example, the sheath 614 may be partially retracted a sufficient distance to expose the second extension leg 530 of the extension graft 500. This may enable a portion of the extension graft 500 (e.g., the extension body 510 and the second extension leg 530) to expand from the radially compressed configuration toward a radially expanded configuration as shown in FIG. 11. The first extension leg 520 may remain compressed within the sheath 614 (e.g., as shown in FIG. 9).

Upon expansion, the extension body 510 of the extension graft 500 may extend through the first fenestration 414a of the main graft 400. In other words, the proximal end 512 of the extension body 510 may be positioned within the lumen 410 of the main graft 400, and the distal end 514 of the extension body may be positioned outside of the lumen of the main graft. Additionally, or alternatively, the extension body 510 of the extension graft 500 may extend at least partially within the first tubular extension 416a of the main graft 400. For example, the proximal end 512 of the extension body 510 may be positioned within the lumen 422a of the first tubular extension 416a or proximal of the second end 420a of the first tubular extension. Upon expansion, the extension body 510 may expand to engage the first tubular extension 416a and/or the sidewall 404 of the main body 402 (e.g., a portion of the sidewall adjacent to the first fenestration 414a). In this manner, a substantially fluid tight seal may be formed between the extension body 510 and the first tubular extension 416a and/or the sidewall 404 to mate the extension graft 500 and the main graft 400 to one another.

The first extension leg 520 of the extension graft 500 may extend outward away from the main graft 400 and toward the innominate artery 308. In one example, the first extension leg 520 may have a sufficiently long length to extend into the innominate artery 308 as shown in FIG. 11. The auxiliary guide wire 620 may be disposed between an outer surface of the first extension leg 520 and the wall of the innominate artery 308. The first extension leg 520 may remain compressed within the sheath 614 of the introducer 600 as described above. In this manner, a space may be formed between the outer surface of the first extension leg 520 and the wall of the innominate artery 308. The auxiliary guide wire 620 may be capable of sliding between the first extension leg 520 and the wall of the innominate artery 308 to retract and remove the auxiliary guide wire from the patient's body as further described below.

Figure 12:
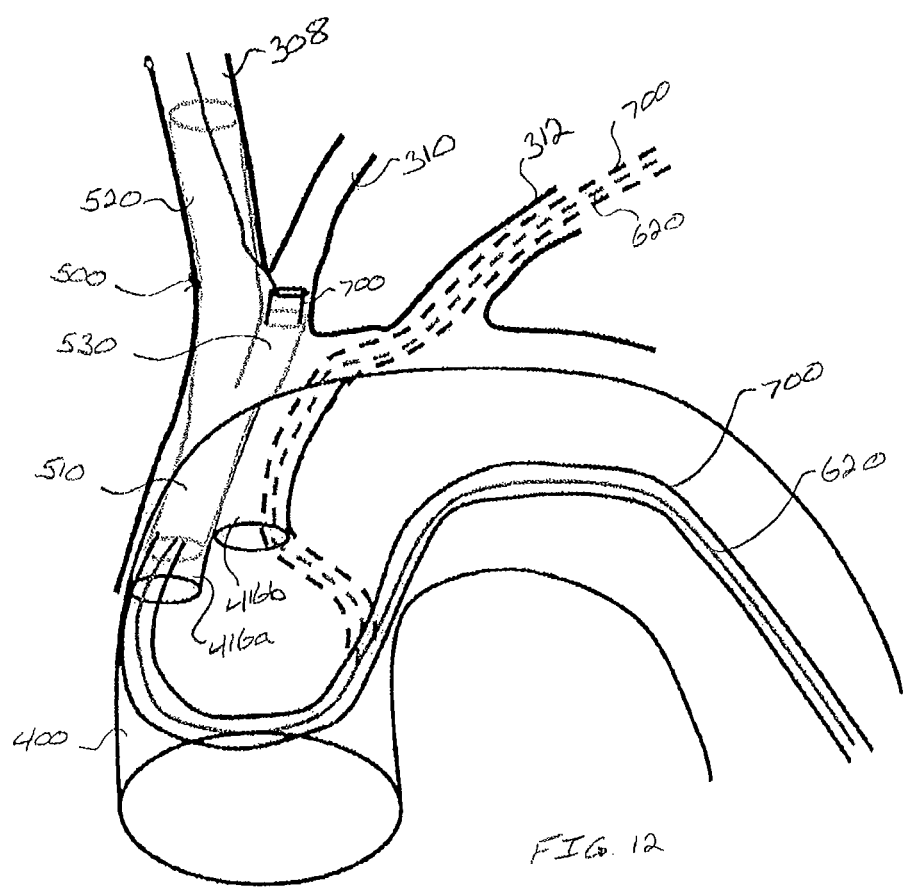
FIGS. 12-13 illustrate deployment of a branch extension graft into the extension graft of FIG. 11.

The second extension leg 530 of the extension graft 500 may extend outward away from the main graft 400 and toward the left common carotid artery 310. In one example, the second extension leg 530 may have a sufficiently short length that the second extension leg does not enter the left common carotid artery 310 as shown in FIG. 11. A branch extension graft may be deployed to couple the second extension leg 530 to the left common carotid artery 310. To that end, a sheath 700 may be advanced over the auxiliary guide wire 620 as shown in FIG. 12. For example, the sheath 700 may be advanced through the abdominal aorta (e.g., via the femoral artery) as shown in solid lines in FIG. 12. The sheath 700 may be advanced proximally through the distal end 408 of the main graft 400, proximally through the lumen 410, and into the lumen 516 of the extension body 510 through the proximal end 512. The sheath 700 may be further advanced into the lumen 536 of the second extension leg 530 and out through the distal end 534. In this manner, the end of the sheath 700 may be positioned adjacent to and/or directed toward the left common carotid artery 310 as shown in FIG. 12.

In another example, the sheath 700 may be advanced through the left subclavian artery 312 as shown in dashed lines in FIG. 12. The sheath 700 may be advanced proximally through the second fenestration 414b and the second tubular extension 416b of the main graft 400, through the lumen 410, and into the lumen 516 of the extension body 510 through the proximal end 512. The sheath 700 may be further advanced into the lumen 536 of the second extension leg 530 and out through the distal end 534. In this manner, the end of the sheath 700 may be positioned adjacent to and/or directed toward the left common carotid artery 310 as shown in FIG. 12.

In another example, the sheath 700 may be advanced through the left ventricle. The sheath 700 may be advanced distally through the proximal end opening into the lumen 410 of the main graft 400, and into the lumen 516 of the extension body 510 through the proximal end 512. The sheath 700 may be further advanced into the lumen 536 of the second extension leg 530 and out through the distal end 534. In this manner, the end of the sheath 700 may be positioned adjacent to and/or directed toward the left common carotid artery 310 as shown in FIG. 12.

Figure 13:
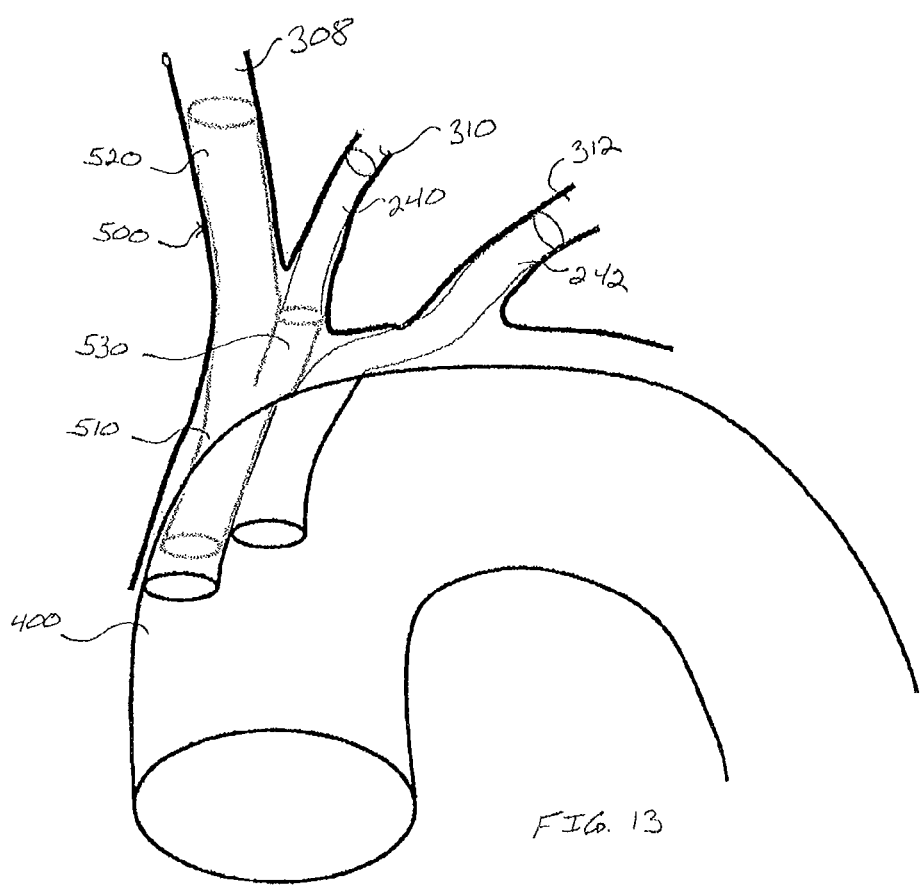

The branch extension graft 240 may be deployed within the extension graft 500 as shown in FIG. 13. The branch extension graft 240 may be deployed via the sheath 700 using any suitable endovascular technique. For example, the branch extension graft 240 may be compressed into a reduced diameter configuration and loaded onto an introducer. The sheath 700 may be positioned with the end of the sheath adjacent to and/or directed toward the left common carotid artery 310 as shown in FIG. 12 and described above. The introducer may be advanced within the sheath 700 and into the left common carotid artery 310. The position of the sheath 700 may aid in directing the introducer into the left common carotid artery 310. With the introducer in position within the left common carotid artery 310, the sheath 700 and the auxiliary guide wire 620 may be retracted and removed from the patient's body. The branch extension graft 240 may be released from the introducer (e.g., by retraction of a sheath of the introducer and/or manipulation of one or more trigger wires or other retention mechanism) to expand and engage the extension graft 500 and/or the walls of the left common carotid artery 310. Upon deployment, the branch extension graft 240 may extend from the second extension leg 530 of the extension graft 500 into the left common carotid artery 310 as shown in FIG. 13. Upon expansion, a first portion of the branch extension graft 240 may engage an inner surface of the second extension leg 530, and a second portion of the branch extension graft may engage the wall of the left common carotid artery 310. In this manner, the extension graft 500 may be coupled to the left common carotid artery 310. A substantially continuous flow path may be established from the lumen 410 of the main graft 400 to the left common carotid artery 310 (e.g., through the lumen 516 of the extension body 510, the lumen 536 of the second extension leg 530, and the lumen of the branch extension graft 240). In this manner, the main graft 400 may be coupled to the left common carotid artery 310.

The sheath 614 of the introducer 600 may be further retracted to deploy the first extension leg 520 of the extension graft 500. Upon expansion, the first extension leg 520 may engage the wall of the innominate artery 308. In this manner, the extension graft 500 may be coupled to the innominate artery 308. A substantially continuous flow path may be established from the lumen 410 of the main graft 400 to the innominate artery 308 (e.g., through the lumen 516 of the extension body and the lumen 526 of the first extension leg 520). In this manner, the main graft 400 may be coupled to the innominate artery 308.

A second branch extension graft 242 may be deployed within the main graft 400 as shown in FIG. 13. The second branch extension graft 242 may be deployed using any suitable endovascular technique. For example, the second branch extension graft 242 may be compressed into a reduced diameter configuration and loaded onto an introducer. The introducer may be advanced proximally through the left subclavian artery 312, through the second fenestration 414b of the main graft 400, and into the second tubular extension 416b. The second branch extension graft 242 may be released from the introducer (e.g., by retraction of a sheath of the introducer and/or manipulation of one or more trigger wires or other retention mechanism) to expand and engage the main graft 400 and/or the walls of the left subclavian artery 312. Upon deployment, the second branch extension graft 242 may extend outward away from the main graft 400 into the left subclavian artery 312 as shown in FIG. 13. Upon expansion, a first portion of the second branch extension graft 242 may engage an inner surface of the second tubular extension 416b, and a second portion of the second branch extension graft may engage the wall of the left subclavian artery 312. In this manner, the main graft 400 may be coupled to the left subclavian artery 312. A substantially continuous flow path may be established from the lumen 410 of the main graft 400 to the left subclavian artery 312 (e.g., through the lumen of the second branch extension 242). In this manner, the main graft 400 may be coupled to the left subclavian artery 312.

The configuration of the extension graft 500 may enable the main graft 400 to be coupled to two branch vessels (e.g., the innominate artery 308 and the left common carotid artery 310) through a single fenestration (e.g., the first fenestration 414a). Coupling the main graft 400 to a third branch vessel (e.g., the left subclavian artery 312) as described above may enable the main graft to be coupled to three branch vessels through two fenestrations (e.g., the first fenestration 414a and the second fenestration 414b). In other words, three branch vessels may be treated with a two-branch device. This may reduce the amount of time required to deploy the prosthesis system. Additionally, or alternatively, this may reduce the obstruction of the lumen 410 of the main graft 400 (e.g., because the ends of only the extension body 510 and the second branch extension graft 242 extend into the lumen of the main body) compared to a three branch device (e.g., a device having three fenestrations and three extension grafts extending into the lumen of the main graft). Additionally, or alternatively, coupling the main graft to each of the three branch vessels (e.g., the innominate artery 308, the left common carotid artery 310, and the left subclavian artery 312) may maintain the blood flow to each of the three branch vessels using endovascular techniques without an invasive surgical procedure (e.g., to place an anastomosis between two of the branch vessels). This may reduce procedural and/or recovery times associated with placement of the prosthesis system.

A patient may have a bovine arch in which the innominate artery and the left common carotid artery share a common origin as opposed to a standard arch in which the innominate artery and the left common carotid artery have *separate* origins. The use of a branched or bifurcated extension graft (e.g., the extension graft 200 or the extension graft 400) as described herein may be preferable for use in a patient having a bovine arch. For example, the fenestration of the main graft (e.g., the fenestration 114 of the main graft 100 or the first fenestration 414a of the main graft 400) may be generally aligned with the common origin of the innominate artery and the left common carotid artery. The first extension leg of the extension graft and the second extension leg of the extension graft may be positioned adjacent to one another in close proximity such that both of the first extension leg and the second extension leg may be directed toward the common origin of the innominate artery and the left common carotid artery.

Figure 14:
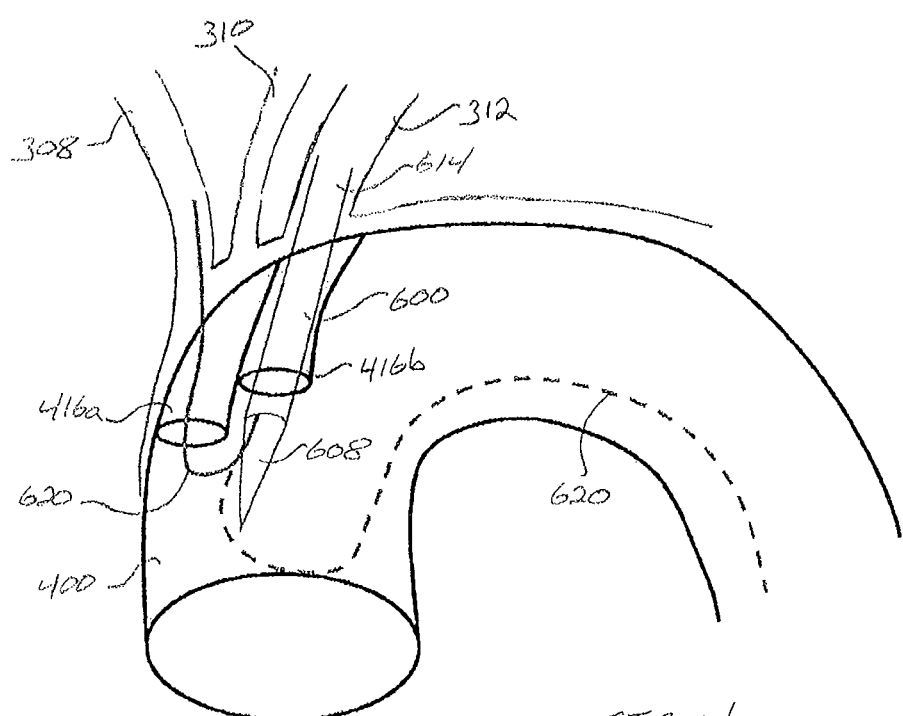
FIG. 14 illustrates the main graft of FIG. 4 deployed within a thoracic aorta of a patient.
Figure 15:
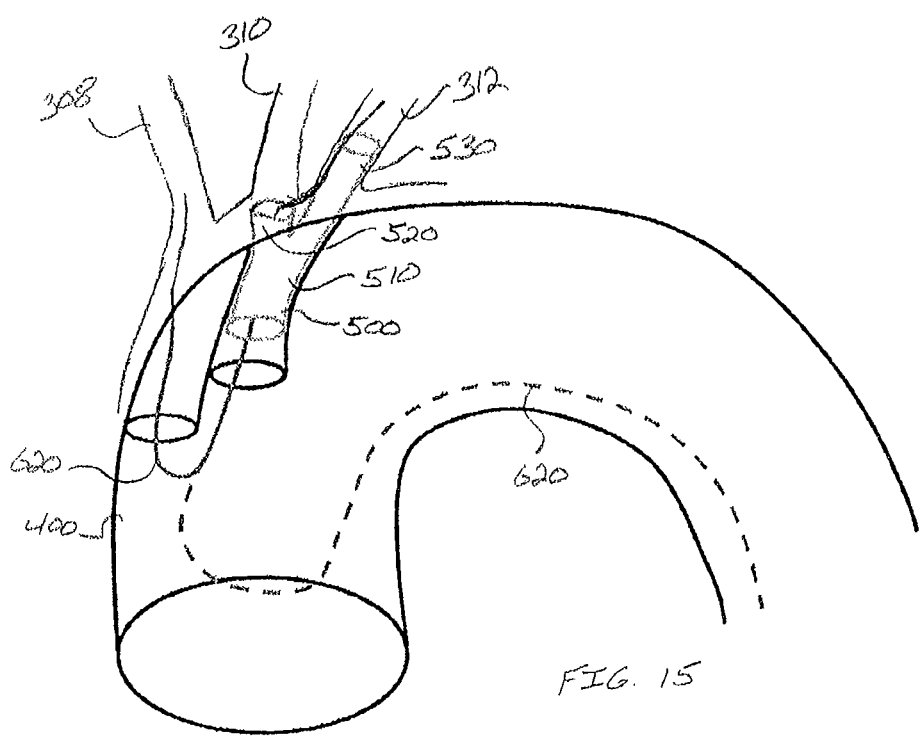
FIG. 15 illustrates one example of the extension graft of FIG. 8 deployed within the main graft of FIG. 14.

FIGS. 14-15 illustrate exemplary steps for deployment of the prosthesis system, including the main graft 400 and the extension graft 500, within the thoracic aorta. The main graft 400 may be deployed within the thoracic aorta using any suitable endovascular technique as described above with reference to FIGS. 10-13. The extension graft 500 may be deployable within the main graft 400 using any suitable endovascular technique. For example, a guide wire may be introduced into the left subclavian artery 312 and advanced proximally through the second fenestration 414b and the second tubular extension 416b of the main graft 400. The guide wire may be further advanced proximally within the lumen 410 of the main graft, out through the proximal end opening, and into the descending aorta 302.

The extension graft 500 may be loaded onto the introducer 600 as described above. The introducer 600 may be introduced over the guide wire and advanced proximally through the left subclavian artery 312. The introducer 600 may be advanced further proximally through the second fenestration 414b and the second tubular extension 416b of the main graft 400 such that the tip 608 of the introducer is disposed within the lumen 410 of the main graft 400 as shown in FIG. 14. The second end of the auxiliary guide wire 620 may be exposed outside of the sheath 614. The auxiliary guide wire 620 may be snared. For example, a snare may be introduced into the innominate artery 308 (e.g., via the axillary artery or the right carotid artery) and advanced into the thoracic aorta to snare the second end of the auxiliary guide wire 620. The second end of the auxiliary guide wire 620 may be pulled distally through the first tubular extension 416a and out through the first fenestration 414a of the main graft 400. This path of the auxiliary guide wire 620 is shown as a solid line in FIG. 14. The second end of the auxiliary guide wire 620 may be pulled out of the patient's body (e.g., via the axillary artery or the right carotid artery). In this manner, the auxiliary guide wire 620 may serve as a through wire with both of the first end and the second end of the auxiliary guide wire positioned outside of the patient's body (e.g., the first end via the left subclavian artery and the second end via the axillary artery or the right carotid artery). With the auxiliary guide wire 620 in place, the auxiliary sheath 618, if used, may be retracted over the auxiliary guide wire and removed from the patient's body (e.g., via the left subclavian artery 312).

In another example, the snare may be introduced into the thoracic aorta (e.g., via the femoral artery) to snare the second end of the auxiliary guide wire 620. The second end of the auxiliary guide wire 620 may be pulled distally through the lumen 410 of the main graft 400 and out through the distal end opening at the distal end 408 of the main graft. This path of the auxiliary guide wire 620 is shown as a dashed line in FIG. 14. The second end of the auxiliary guide wire 620 may be pulled out of the patient's body (e.g., via the femoral artery). In this manner, the auxiliary guide wire 620 may serve as a through wire with both of the first end and the second end of the auxiliary guide wire positioned outside of the patient's body (e.g., the first end via the left subclavian artery 312 and the second end via the femoral artery).

In another example, the snare may be introduced into the thoracic aorta via the apex of the left ventricle to snare the second end of the auxiliary guide wire 620. The second end of the auxiliary wire 620 may be pulled proximally through the proximal end opening of the main graft 400 and out of the patient's body via the left ventricle. In this manner, the auxiliary guide wire 620 may serve as a through wire with both of the first end and the second end of the auxiliary guide wire positioned outside of the patient's body (e.g., the first end via the left subclavian artery 312 and the second end via the left ventricle).

The extension graft 500 may be deployed within the main graft 500 as described above. Upon expansion, the extension body 510 of the extension graft 500 may extend through the second fenestration 414b of the main graft 400 as shown in FIG. 15. Upon expansion, the extension body 510 may expand to engage the second tubular extension 416b and/or the sidewall 404 of the main body 402 to mate the extension graft 500 and the main graft 400 to one another.

The first extension leg 520 of the extension graft 500 may extend outward away from the main graft 400 and toward and/or into the left subclavian artery 312. The first extension leg 520 may remain compressed within the sheath 614 as described above with reference to FIGS. 10-13. The second extension leg 530 of the extension graft 500 may extend outward away from the main graft 400 and toward the left common carotid artery 310 as shown in FIG. 15. The branch extension graft 240 may be used to couple the second extension leg 530 to the left common carotid artery 310 as described above with reference to FIGS. 10-13 (e.g., using the sheath 700 advanced over the auxiliary guide wire 620 and the introducer advanced within the sheath). The sheath 614 may be further retracted to enable expansion of the first extension leg 520. Upon expansion, the first extension leg 520 may engage the wall of the left subclavian artery 312 to couple the extension graft 500 to the left subclavian artery as shown in FIG. 15. A substantially continuous flow path may be established from the lumen 410 of the main graft 400 to the subclavian artery 312 (e.g., through the lumen 516 of the extension body and the lumen 526 of the first extension leg 520) to couple the main graft 400 to the left subclavian artery.

The second branch extension graft may be deployed within the main graft 400 as described above with reference to FIGS. 10-13. For example, the second branch extension graft may be compressed into a reduced diameter configuration and loaded onto the introducer. The introducer may be advanced proximally through the innominate artery 308, through the first fenestration 414a of the main graft 400, and into the first tubular extension 416a. Upon deployment, the second branch extension graft may extend outward away from the main graft 400 into the innominate artery 308 to couple the main graft 400 to the innominate artery 308.

In any of the examples described herein, the prosthesis system and/or various components thereof may be sized and shaped for placement at a desired position within a patient's anatomy. For example, the extension graft (e.g., the extension graft 200 and/or the extension graft 500) may have a diameter at the proximal end ranging from about 10 mm to about 16 mm, typically from about 12 mm to about 14 mm, preferably about 13 mm. The extension graft may have a diameter at the distal end ranging from about 12 mm to about 26 mm, typically from about 16 mm to about 24 mm. The first extension leg and/or the second extension leg may have a diameter ranging from about 5 mm to about 11 mm, typically from about 7 mm to about 9 mm, preferably about 8 mm. The extension body may have a length ranging from about 22 mm to about 28 mm, typically from about 24 mm to about 26 mm, preferably about 25 mm. Additionally, or alternatively, the branch ostium may begin about 25 mm distal to the proximal end of the extension body. To that end, the distance between the proximal end of the extension body and the proximal end of the second extension leg may be about 25 mm. The support structure of the extension body may include three low profile stents. The stents may be disposed on an inner surface of the sidewall of the extension body. Alternatively the support structure of the extension body may include any number stents (e.g., one, two, four, or more), and the stents may be disposed on the inner surface and/or the outer surface of the extension body. Additionally, or alternatively, the fenestration of the main graft (e.g., the fenestration 114 of the main graft 100, the first fenestration 114a of the main graft 400, and/or the second fenestration 114b of the main graft 400) may have a diameter ranging from about 6 mm to about 14 mm, typically from about 8 mm to about 12 mm.

In any of the examples described herein, the support structures may include one or more stents having any suitable stent pattern known in the art. The stents may be balloon expandable and/or self-expandable. One example of a stent pattern is the Z-stent or Gianturco stent design. Each Z-stent may include a series of substantially straight segments or struts interconnected by a series of bent segments or bends. Alternative stent designs may include, for example, annular stents, helical stents, a woven wire structure, a laser-cut cannula, individual interconnected rings, or another pattern or design.

The support structures may be made from any suitable material known in the art. In one example, the support structures may be made from standard medical grade stainless steel and may be soldered using silver standard solder (0 lead/0 tin). In other examples, the support structures may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide (La2O3), a nickel-titanium alloy, or other suitable materials known in the art. Additionally, or alternatively, the stents may be made from nitinol or other superelastic or shape-memory metal.

In any of the examples described herein, the grafts may be made of any suitable biocompatible graft material known in the art. For example, the graft bodies may be made of an expanded polytetrafluoroethylene (ePTFE), polytetrafluoroethylene (PTFE), silicone, polyurethane, polyester, polyamide (nylon), polyethylene, polypropylene, polyaramid, polyacrylonitrile, cellulose, or another flexible biocompatible material. Additionally, or alternatively, the graft bodies may include a bioremodelable material such as reconstituted or naturally-derived collagenous materials such as, for example, collagenous extracellular matrix (ECM) materials such as those including submucosa, renal capsule membrane, dermal collagen, dura mater, pericardium, fascia lata, serosa, peritoneum or basement membrane layers, including liver basement membrane. Suitable submucosa materials may include, for example, intestinal submucosa including small intestinal submucosa, stomach submucosa, urinary bladder submucosa, and uterine submucosa. For additional information as to some of the materials which may be useful in the present invention, and their isolation and treatment, reference may be made, for example, to U.S. Pat. Nos. 4,902,508, 5,554,389, 5,993,844, 6,206,931, and 6,099,567. Non-limiting examples of suitable remodelable materials may include SURGISIS® BIODESIGN™ from Cook Medical (Bloomington, Ind.) or the graft prosthesis material described in U.S. Pat. No. 6,206,931 to Cook et al., which is incorporated herein by reference in its entirety. Additionally, or alternatively, the graft materials may include any of the materials described in U.S. Pat. No. 7,407,509 to Greenberg et al. or U.S. Patent Application Pub. No. 2009/0171451 by Kuppurathanam et al., which are incorporated herein by reference in their entirety.

While various embodiments of the invention have been described, the invention is not to be restricted except in light of the attached claims and their equivalents. Drawings in the figures illustrating various embodiments are not necessarily to scale. Some drawings may have certain details magnified for emphasis, and any different numbers or proportions of parts should not be read as limiting unless so-designated in the present disclosure. Those skilled in the art will appreciate that embodiments not expressly illustrated herein may be practiced within the scope of the present invention, including those features described herein for different embodiments, which may be combined with each other and/or with currently-known or future-developed technologies while remaining within the scope of the claims presented herein. Moreover, the advantages described herein are not necessarily the only advantages of the invention and it is not necessarily expected that every embodiment of the invention will achieve all of the advantages described.

The invention claimed is:

1. An endoluminal prosthesis system comprising:
a main graft comprising a tubular main body having an open proximal end, an open distal end, a sidewall, a main graft lumen extending longitudinally between the proximal end and the distal end, a first recess in the side wall having a proximal end, a distal end, at least one proximal side, and at least one distal side, a second recess in the side wall longitudinally and circumferentially offset from the first recess and having a proximal end, a distal end, at least one proximal side, and at least one distal side, a first fenestration in the sidewall between the proximal open end and the distal open end and disposed within the first recess at the proximal end of the first recess, and a second fenestration in the side wall between the proximal open and the distal open end and disposed within the second recess at the proximal end of the second recess,
wherein a proximal side of the second recess abuts a distal side of the first recess;
a first internal tube disposed within the main graft lumen and extending from the first fenestration, the first internal tube having a first open end at the first fenestration and a second open end extending toward the main body open proximal end, a second internal tube disposed within the main graft lumen and extending from the second fenestration, the second internal tube having a first open at the second fenestration and a second open end extending toward the main body open proximal end;
and
a first extension graft comprising, as a single piece a tubular extension body, a tubular first extension leg, and a tubular second extension leg, the extension body comprising an open first end, a second end, and a lumen extending longitudinally between the first end and the second end, each of the first extension leg and the second extension leg extending from the second end of the extension body to form a point of bifurcation at the second end of the extension body and each comprising a first end, a second end, and a lumen in fluid communication with the lumen of the extension body, wherein one of the first and second extension legs is longer than the other;
wherein the first extension graft is deployable within the main graft such that the extension body extends through the fenestration in the sidewall of the main body and into the first internal tube and each of the first extension leg and the second extension leg extends outwardly away from the sidewall of the main graft, and wherein a second extension graft is deployable within the main graft such that the second extension graft extends through the second fenestration in the sidewall of the main body and into the second internal tube.

2. The system of claim 1, wherein the first extension graft is deployable within the main graft such that an outer surface of the extension body engages an inner surface of the internal tube.

3. The system of claim 1, wherein the fenestration of the main graft comprises a first fenestration in the sidewall and a second fenestration in the sidewall distal of the first fenestration.

4. The system of claim 3, wherein the extension graft is deployable within the main graft such that the extension graft extends through one of the first fenestration or the second fenestration, and the system further comprises a branch extension graft deployable within the main graft such that the branch extension graft extends through the other of the first fenestration or the second fenestration.

5. The system of claim 1, wherein the first extension leg is longer than the second extension leg.

6. The system of claim 1, wherein the extension graft is deployable within the main graft such that the lumen of the main body is in fluid communication with each of the lumen of the first extension leg and the lumen of the second extension leg through the fenestration.

7. An endoluminal prosthesis system comprising:
a main graft comprising a tubular main body having an open proximal end, an open distal end, a sidewall, a main graft lumen extending longitudinally between the proximal end and the distal end, a diamond shaped recess disposed in the side wall and a having first and second proximal sides, a proximal apex, first and second distal sides and a distal apex, and a fenestration disposed in the diamond shaped recess at the proximal apex of the diamond shaped recess;
an internal tube disposed within the main graft lumen extending from the fenestration, the internal tube having a first open end at the fenestration and a second open end extending toward the main body open proximal end; and
an extension graft comprising, as a single piece, a tubular extension body, a tubular first extension leg, and a tubular second extension leg, the extension body comprising an open first end, a second end, and a lumen extending longitudinally between the first end and the second end, and each of the first and second tubular extension legs comprising a first end, a second end, and a lumen in fluid communication with the lumen of the extension body;
wherein the extension graft is deployable within the main graft such that the extension body extends through the fenestration in the sidewall of the main body and into the internal tube and each of the first extension leg and the second extension leg extends outwardly away from the sidewall of the main graft.

8. An endoluminal prosthesis system comprising:
a main graft comprising a tubular main body comprising a sidewall, an open proximal end, an open distal end, a main graft lumen extending longitudinally between the proximal end and the distal end, a first recess in the side wall, a second recess in the sidewall longitudinally and circumferentially offset from the first recess and abutting the first recess, and a first fenestration in the first recess of the sidewall and a second fenestration in the second recess of the sidewall;
at least one internal tube disposed within the main graft lumen extending from the first fenestration, the internal tube having a first open end at the first fenestration and a second open end extending toward the main body open proximal end;
an extension graft comprising, as a single piece, a tubular extension body, a tubular first extension leg, and a tubular second extension leg, the extension body comprising an open first end, a second end, and a lumen extending longitudinally between the first end and the second end, each of the first extension leg and the second extension leg extending from the extension body and comprising a first end, a second end, and a lumen in fluid communication with the lumen of the extension body; and an auxiliary guide preloaded with and disposed in the extension graft and extending through each of the lumen of the second extension leg and the lumen of the extension body, wherein the auxiliary guide is disposed within the extension graft prior to introduction into a patient;

wherein, the extension graft is positionable within the main graft such that the extension body extends through the first fenestration in the sidewall of the main body and into the at least one internal tube, each of the first extension leg and the second extension leg extends outwardly away from an exterior of the main graft, and an end of the auxiliary guide is disposed within the lumen of the main graft.

9. The system of claim 8, further comprising an introducer comprising an elongate cannula, a handle disposed at a first end of the cannula, and a tip disposed at a second end of the cannula;

wherein the extension graft is loaded on the introducer such that the elongate cannula of the introducer extends through each of the lumen of the first extension leg and the lumen of the extension body, and wherein the second end of each of the first extension leg and the second extension leg is directed toward the handle of the introducer, and the first end of the extension body is directed toward the tip of the introducer.

10. The system of claim 9, wherein the end of the auxiliary guide is disposed at the tip of the introducer.

11. The system of claim 8, wherein the auxiliary guide comprises an auxiliary cannula preloaded in the extension graft, extending into the extension graft at the second end of the second extension leg, and exiting the extension graft at the first end of the extension body, and wherein the auxiliary guide is configured to receive an auxiliary guide wire.

12. The system of claim 8, wherein the extension body comprises a support structure attached to an inner surface of the extension body, and the extension body is deployable within the main graft such that an outer surface of the extension body engages an inner surface of the internal tube.

13. The system of claim 8, wherein the at least one internal tube comprises a first internal tube fluidly coupled to the first fenestration and disposed within the lumen of the main graft and a second internal tube fluidly coupled to the second fenestration and disposed within the lumen of the main graft adjacent to the first internal tube.

14. A method of deploying a prosthesis system, the method comprising:

deploying a main graft comprising a tubular main body comprising a sidewall, an open proximal end, an open distal end, a lumen extending longitudinally between the proximal end and the distal end, a first recess in the sidewall, a second recess in the sidewall longitudinally and circumferentially offset from the first recess and abutting the first recess, a fenestration in the first recess in the sidewall, a second fenestration in the second recess of the side wall, and an internal tube disposed within the main graft lumen extending from the first fenestration, the internal tube having a first open end at the first fenestration and a second open end extending toward the main body open proximal end;

deploying an extension graft within the main graft, the extension graft comprising, as a single piece, a tubular extension body disposed through the first fenestration of the main graft and into the internal tube, a tubular first extension leg, and a tubular second extension leg, each of the first extension leg and the second extension leg extending from the extension body outwardly away from an exterior of the side wall of the main graft;

snaring an end of an auxiliary guide wire disposed within the lumen of the main graft, the auxiliary guide wire extending through a lumen of the extension body and a lumen of the second extension leg;

advancing an introducer over the end of the auxiliary guide wire and into the second extension leg; and deploying a branch extension graft within the second extension leg with the introducer.

* * * * *